(12) United States Patent
Leon et al.

(10) Patent No.: US 7,807,882 B2
(45) Date of Patent: Oct. 5, 2010

(54) HERBICIDE-RESISTANT SUNFLOWER PLANTS, POLYNUCLEOTIDES ENCODING HERBICIDE-RESISTANT ACETOHYDROXYACID SYNTHASE LARGE SUBUNIT PROTEINS, AND METHODS OF USE

(75) Inventors: Alberto Javier Leon, Mar del Plata (AR); Monica Mariel Morata, Mar del Plata (AR); Andres D. Zambelli, Mar del Plata (AR)

(73) Assignees: BASF Agrochemical Products B.V., Arnhem (NL); Advanta Seeds B.V., Kapelle (NL)

( * ) Notice: Subject to any disclaimer, the term of this patent is extended or adjusted under 35 U.S.C. 154(b) by 500 days.

(21) Appl. No.: 11/659,007

(22) PCT Filed: Jul. 29, 2005

(86) PCT No.: PCT/EP2005/008265

§ 371 (c)(1),
(2), (4) Date: Jun. 29, 2007

(87) PCT Pub. No.: WO2006/024351

PCT Pub. Date: Mar. 9, 2006

(65) Prior Publication Data

US 2007/0300321 A1 Dec. 27, 2007

Related U.S. Application Data

(60) Provisional application No. 60/592,471, filed on Jul. 30, 2004.

(51) Int. Cl.
*A01H 1/00* (2006.01)
*A01H 5/00* (2006.01)
*A01H 5/10* (2006.01)
*C12N 15/82* (2006.01)

(52) U.S. Cl. .................. 800/300; 800/260; 800/266; 800/322

(58) Field of Classification Search .............. None
See application file for complete search history.

(56) References Cited

U.S. PATENT DOCUMENTS 5,116,402 A * 5/1992 Dutka et al. ............... 504/108
6,175,065 B1 * 1/2001 Schmidt et al. ............ 800/322

OTHER PUBLICATIONS

Bernasconi et al 1995, The Journal of Biological Chemistry 207(29): 17381-17385.*
PI 633749 deposited Jul. 11, 2003, USDA, ARS, National Genetics Resources Program. Germplasm Resources Information Network—(GRIN). [Online Database] National Germplasm Resources Laboratory, Beltsville, Maryland.*
Miller et al, May 1, 2004, Crop Science 44:1037-1038.*
Baumgartner et al, 1999, Weed Technology 13(3): 489-493.*
Kolkman et al, 2004, Theor. Appl. Genet. 109: 1147-1159.*
Guttieri, M. J. et al. "Diverse Mutations in the Acetolactate Synthase Gene Confer Chlorsulfuron Resistance in Kochia (*Kochia scoparia*) Biotypes" *Weed Science,* 1995, pp. 175-178, vol. 43.
Guttieri, M. J. et al. "DNA Sequence Variation in Domain A of the Acetolactate-Susceptible Weed Biotypes" *Weed Science,* 1992, pp. 670-676, vol. 40.
Boutsalis, P. et al. "Molecular Basis of Resistance to Acetolactate Synthase-Inhibiting Herbicides in Sisymbrium Orientale and Brassica Tournefortii" *Pesticide Science,* 1999, pp. 507-516, vol. 55.
White, A. D. et al., "Common Sunflower Resistance to Acetolactate Synthase-Inhibiting Herbicides" *Weed Science,* 2002, pp. 432-437, vol. 50.
White, A. D. et al., "Isolation of Acetolactatet Synthase Homologs in Common Sunflowers" *Weed Science,* 2003, pp. 845-853, vol. 51.

* cited by examiner

*Primary Examiner*—David H Kruse
(74) *Attorney, Agent, or Firm*—Womble Carlyle Sandridge & Rice PLLC

(57) ABSTRACT

Herbicide-resistant sunflower plants, isolated polynucleotides that encode herbicide resistant and wild type acetohydroxyacid synthase large subunit (AHASL) polypeptides, and the amino acid sequences of these polypeptides, are described. Expression cassettes and transformation vectors comprising the polynucleotides of the invention, as well as plants and host cells transformed with the polynucleotides, are described. Methods of using the polynucleotides to enhance the resistance of plants to herbicides, and methods for controlling weeds in the vicinity of herbicide-resistant plants are also described.

21 Claims, 6 Drawing Sheets

FIGURE 1

|  |  | Start | 50 |
|---|---|---|---|
| 1248-3 | (1) | ATGGCGGC------TCCTCCCAACCCTTCCATCTCCTTCAAACCACCGTC | |
| HA89 | (1) | ATGGCGGC------TCCTCCCAACCCTTCCATCTCCTTCAAACCACCGTC | |
| Xanthium | (1) | ATGGCGGCCATCCCTCATACAAACCCTTCCATCACCACCAAACCACCCTC | |
|  |  | 51 | 100 |
| 1248-3 | (45) | ACCCGCCGCCGCACTGCCACCACGCTCCGCCTTCCTCCCCCGTTTCGCAT | |
| HA89 | (45) | ACCCGCCGCCGCACTGCCACCACGCTCCGCCTTCCTCCCCCGTTTCGCAT | |
| Xanthium | (51) | ATCT-----------CCACCACGTCCCACCTTCCTCGCCCGTTTCACAT | |
|  |  | 101 | 150 |
| 1248-3 | (95) | TACCCATCACTTCCACTACCCAAAAACGACACCGTCTTCACATCTCCAAT | |
| HA89 | (95) | TACCCATCACTTCCACTACCCAAAAACGACACCGTCTTCACATCTCCAAT | |
| Xanthium | (89) | TCCCAATAACCTCCACTTCCCATAAACGACACCGTCTCCACATCTCCAAC | |
|  |  | 151 | 200 |
| 1248-3 | (145) | GTTCTCTCCGACTCCAAATCCACCACCACCACCACCACCACCACTCAACG | |
| HA89 | (145) | GTTCTCTCCGACTCCAAATCCACCACCACCACCACCACCACCACTCAACG | |
| Xanthium | (139) | GTCCTCTCCGACTCCAAACCCACCATCAC----------CCATTCA--- | |
|  |  | 201 | 250 |
| 1248-3 | (195) | ACCGTTACCGGTGCAGCCTTTTGTCTCCCGTTACGCGCCAGATCAACCGA | |
| HA89 | (195) | ACCGTTACCGGTGCAGCCTTTTGTCTCCCGTTACGCGCCAGATCAACCGA | |
| Xanthium | (175) | -CCATTACCAACCGAATCATTTATCTCCCGTTACGCTCCAGACCAACCAA | |
|  |  | 251 | 300 |
| 1248-3 | (245) | GAAAAGGCGCAGACGTGTTGGTGGAAGCTCTGGAACGGGAAGGTGTCACC | |
| HA89 | (245) | GAAAAGGCGCAGACGTGTTGGTGGAAGCTCTGGAACGGGAAGGTGTCACC | |
| Xanthium | (224) | GAAAAGGCGCTGATGTTCTCGTCGAAGCTCTGGAACGTGAAGGCGTTACA | |
|  |  | 301 | 350 |
| 1248-3 | (295) | GACGTCTTCGCCTACCCCGGCGGCGCGTCAATGGAGATCCACCAAGCTCT | |
| HA89 | (295) | GACGTCTTCGCCTACCCCGGCGGCGCGTCAATGGAGATCCACCAAGCTCT | |
| Xanthium | (274) | GACGTCTTCGCTTACCCAGGTGGTGCCTCCATGGAGATCCACCAAGCTCT | |
|  |  | 351 | 400 |
| 1248-3 | (345) | CACGCGCTCAAGCACTATCCGCAATGTGCTCCCCCGTCACGAACAGGGCG | |
| HA89 | (345) | CACGCGCTCAAGCACTATCCGCAATGTGCTCCCCCGTCACGAACAGGGCG | |
| Xanthium | (324) | CACGCGCTCAACCACCATCCGCAACGTTCTCCCACGTCACGAACAGGGCG | |
|  |  | 401 | 450 |
| 1248-3 | (395) | GCGTGTTCGCCGCCGAAGGCTACGCGCGCGCCTCCGGTCTTCCCGGCGTG | |
| HA89 | (395) | GCGTGTTCGCCGCCGAAGGCTACGCGCGCGCCTCCGGTCTTCCCGGCGTG | |
| Xanthium | (374) | GCGTCTTTGCTGCCGAAGGCTACGCACGTGCCTCCGGTCTTCCCGGCGTC | |
|  |  | 451 | 500 |
| 1248-3 | (445) | TGTATCGCCACTTCCGGTCCCGGAGCTACGAACCTAGTTAGTGGTCTTGC | |
| HA89 | (445) | TGTATCGCCACTTCCGGTCCCGGAGCTACGAACCTAGTTAGTGGTCTTGC | |
| Xanthium | (424) | TGTATTGCAACCTCTGGTCCTGGAGCTACGAACCTAGTAAGTGGTCTTGC | |
|  |  | 501 | 550 |
| 1248-3 | (495) | TGACGCGCTGTTAGACAGTGTCCCCATGGTGGCAATCACCGGTCAAGTTC | |
| HA89 | (495) | TGACGCGCTGTTAGACAGTGTCCCCATGGTGGCAATCACCGGTCAAGTTC | |
| Xanthium | (474) | TGATGCTTTATTAGACAGTGTTCCAATGGTTGCTATTACTGGTCAAGTTC | |

FIGURE 1

```
                        * transition C→T                              600
1248-3     (545)   TCCGGAGAATGATCGGAACCGATGCGTTTCAAGAAACCCCAATTGTTGAG
  HA89     (545)   CCCGGAGAATGATCGGAACCGATGCGTTTCAAGAAACCCCAATTGTTGAG
Xanthium   (524)   CCAGGAGAATGATTGGAACAGATGCGTTTCAAGAAACCCCTATTGTTGAG
                   601                                                650
1248-3     (595)   GTAACACGTTCGATCACTAAACATAATTATCTTGTGTTGGATGTTGAGGA
  HA89     (595)   GTAACACGTTCGATCACTAAACATAATTATCTTGTGTTGGATGTTGAGGA
Xanthium   (574)   GTAACACGTTCCATTACTAAGCATAATTATTTAGTTTTGGATGTCGAGGA
                   651                                                700
1248-3     (645)   TATTCCCAGAATTGTTCGTGAGGCTTTTTATCTTGCGAGTTCGGGTCGAC
  HA89     (645)   TATTCCCAGAATTGTTCGTGAGGCTTTTTATCTTGCGAGTTCGGGTCGAC
Xanthium   (624)   TATTCCCAGGATTGTTAGGGAAGCTTTTTATCTTGCGTCTTCTGGTCGAC
                   701                                                750
1248-3     (695)   CCGGCCCGGTTTTGATAGATGTACCGAAAGATATACAGCAACAGTTAGTG
  HA89     (695)   CCGGCCCGGTTTTGATAGATGTACCGAAAGATATACAGCAACAGTTAGTG
Xanthium   (674)   CCGGACCGGTTTTAATTGATGTACCTAAGGATATACAGCAGCAGTTGGTA
                   751                                                800
1248-3     (745)   GTGCCGAAATGGGATGAACCGATGAGGTTACCGGGTTATTTGTCTAGAAT
  HA89     (745)   GTGCCGAAATGGGATGAACCGATGAGGTTACCGGGTTATTTGTCTAGAAT
Xanthium   (724)   GTGCCTAAATGGGATGAGCCTATTAGGTTACCTGGGTATTTGTCTAGGTT
                   801                                                850
1248-3     (795)   GCCGAAGCCTCAATATGATGGGCATTTGGAACAGATTGTTAGGTTGGTGG
  HA89     (795)   GCCGAAGCCTCAATATGATGGGCATTTGGAACAGATTGTTAGGTTGGTGG
Xanthium   (774)   GCCTAAAACGGAGAATAATGGGCAGTTGGAACACATTGTTAGGTTGGTGA
                   851                                                900
1248-3     (845)   GGGAAGCGAAGAGGCCGGTTTTGTATGTGGGTGGTGGGTGTTTGAATTCG
  HA89     (845)   GGGAAGCGAAGAGGCCGGTTTTGTATGTGGGTGGTGGGTGTTTGAATTCG
Xanthium   (824)   GTGAGGCCAAGAGGCCGGTTTTGTATGTGGGGGGTGGGTGTTTGAATTCG
                   901                                                950
1248-3     (895)   GATGATGAGTTGAGGCGGTTTGTGGAGCTTACGGGGATTCCGGTTGCGAG
  HA89     (895)   GATGATGAGTTGAGGCGGTTTGTGGAGCTTACGGGGATTCCGGTTGCGAG
Xanthium   (874)   GGAGATGAGTTGAGGCGGTTTGTGGAGCTTACGGGGATACCGGTTGCGAG
                   951                                               1000
1248-3     (945)   TACTTTGATGGGGCTCGGAGCGTACCCTGCTTCGAGTGATTTGTCGCTTC
  HA89     (945)   TACTTTGATGGGGCTCGGAGCGTACCCTGCTTCGAGTGATTTGTCGCTTC
Xanthium   (924)   TACGTTGATGGGGCTTGGAGCGTACCCTGCTTCTAGTGATTTGTCGCTGC
                   1001                                              1050
1248-3     (995)   ATATGCTTGGGATGCATGGTACGGTTTATGCGAATTATGCGGTTGATAAG
  HA89     (995)   ATATGCTTGGGATGCATGGTACGGTTTATGCGAATTATGCGGTTGATAAG
Xanthium   (974)   ATATGCTTGGGATGCATGGACGGTTTATGCGAATTATGCGGTTGATAAG
                   1051                                              1100
1248-3    (1045)   AGTGATTTGTTGCTTGCGTTTGGGGTGCGGTTTGATGATCGTGTGACGGG
  HA89    (1045)   AGTGATTTGTTGCTTGCGTTTGGGGTGCGGTTTGATGATCGTGTGACGGG
Xanthium  (1024)   AGTGATTTGTTGCTTGCGTTTGGGGTAAGGTTTGATGACCGTGTGACGGG
```

FIGURE 1

|  |  | 1101 | 1150 |
|---|---|---|---|
| 1248-3 | (1095) | GAAGCTTGAGGCGTTTGCTAGTAGGGCGAAGATTGTTCATATTGATATTG | |
| HA89 | (1095) | GAAGCTTGAGGCGTTTGCTAGTAGGGCGAAGATTGTTCATATTGATATTG | |
| Xanthium | (1074) | GAAGCTTGAGGCTTTTGCTAGCAGAGCTAAGATTGTTCATATTGATATTG | |
|  |  | 1151 | 1200 |
| 1248-3 | (1145) | ATCCTGCTGAAATTGGGAAGAATAAGCAGCCTCATGTGTCGATTTGTGGT | |
| HA89 | (1145) | ATCCTGCTGAAATTGGGAAGAATAAGCAGCCTCATGTGTCGATTTGTGGT | |
| Xanthium | (1124) | ATTCTGCGGAAATTGGGAAGAATAAGCAGCCTCATGTGTCGATTTGTGGT | |
|  |  | 1201 | 1250 |
| 1248-3 | (1195) | GATATTAAGGTCGCGTTACAGGGTTTGAACAAGATTTTGGAGGAAAAGAA | |
| HA89 | (1195) | GATATTAAGGTCGCGTTACAGGGTTTGAACAAGATTTTGGAGGAAAAGAA | |
| Xanthium | (1174) | GATATCAAGGTCGCGTTACAGGGTCTGAACAAGATTTTGGAGGTAAAGAA | |
|  |  | 1251 | 1300 |
| 1248-3 | (1245) | TTCGGTGACTAATCTTGATTTTTCGACCTGGAGAAAGGAATTGGATGAAC | |
| HA89 | (1245) | TTCGGTGACTAATCTTGATTTTTCGACCTGGAGAAAGGAATTGGATGAAC | |
| Xanthium | (1224) | TTCGGTGACTAATCTTGATTTCTCGAACTGGAGGAAGGAATTGGATGAGC | |
|  |  | 1301 | 1350 |
| 1248-3 | (1295) | AAAAAATGAAGTTCCCGTTGAGCTTTAAAACGTTTGGCGAAGCGATTCCT | |
| HA89 | (1295) | AAAAAATGAAGTTCCCGTTGAGCTTTAAAACGTTTGGCGAAGCGATTCCT | |
| Xanthium | (1274) | AAAAGGTTAAGTATCCGTTGAGTTTTAAAACATTTGGCGAAGCTATTCCT | |
|  |  | 1351 | 1400 |
| 1248-3 | (1345) | CCACAGTATGCTATTCAAGTTCTTGATGAGTTAACGGGCGGGAATGCAAT | |
| HA89 | (1345) | CCACAGTATGCTATTCAAGTTCTTGATGAGTTAACGGGCGGGAATGCAAT | |
| Xanthium | (1324) | CCGCAGTATGCCATTCAAGTGCTTGATGAGTTAACGGGTGGGAATGCGAT | |
|  |  | 1401 | 1450 |
| 1248-3 | (1395) | TATTAGCACCGGTGTCGGGCAACATCAGATGTGGGCTGCTCAGTTTTACA | |
| HA89 | (1395) | TATTAGCACCGGTGTCGGGCAACATCAGATGTGGGCTGCTCAGTTTTACA | |
| Xanthium | (1374) | TATTAGCACTGGGGTCGGGCAGCATCAGATGTGGGCTGCTCAGTTTTACA | |
|  |  | 1451 | 1500 |
| 1248-3 | (1445) | AATACAACAAACCTAGACAATGGCTGACGTCGGGCGGGCTAGGGGCAATG | |
| HA89 | (1445) | AATACAACAAACCTAGACAATGGCTGACGTCGGGCGGGCTAGGGGCAATG | |
| Xanthium | (1424) | AATACAACAAGCCTAGACAATGGCTGACGTCAGGTGGACTAGGCGCGATG | |
|  |  | 1501 | 1550 |
| 1248-3 | (1495) | GGTTTCGGCCTGCCCGCTGCTATCGGGCGGCCGTTGCAAGACCTGATGC | |
| HA89 | (1495) | GGTTTCGGCCTGCCCGCTGCTATCGGGCGGCCGTTGCAAGACCTGATGC | |
| Xanthium | (1474) | GGTTTTGGGTTGCCCGCTGCTATCGGGCGGCTGTTGCAAGACCTGATGC | |
|  |  | 1551 | 1600 |
| 1248-3 | (1545) | GGTAGTAGTTGACATCGACGGTGACGGAAGCTTTATGATGAATGTTCAAG | |
| HA89 | (1545) | GGTAGTAGTTGACATCGACGGTGACGGAAGCTTTATGATGAATGTTCAAG | |
| Xanthium | (1524) | GGTAGTAGTTGATATCGATGGTGATGGAAGCTTTATAATGAGCGTTCAAG | |
|  |  | 1601 | 1650 |
| 1248-3 | (1595) | AGTTAGCCACAATCCGTGTTGAAAATCTGCCGGTTAAGATTTTATTACTT | |
| HA89 | (1595) | AGTTAGCCACAATCCGTGTTGAAAATCTGCCGGTTAAGATTTTATTACTT | |
| Xanthium | (1574) | AGTTAGCCACAATCCGTGTTGAAAATCTTCCTGTTAAGATTTTGTTACTT | |

FIGURE 1

```
              1651                                              1700
1248-3  (1645) AACAACCAGCATTTGGGTATGGTGGTTCAGTGGGAGGATCGGTTTTACAA
  HA89  (1645) AACAACCAGCATTTGGGTATGGTGGTTCAGTGGGAGGATCGGTTTTACAA
Xanthium (1624) AACAATCAGCATTTGGGTATGGTGGTTCAGTTGGAGGATCGGTTTTACAA
              1701                                              1750
1248-3  (1695) GGCGAATCGGGCTCATACCTACTTAGGAAACCCGTCAAAAGAGTCGGAAA
  HA89  (1695) GGCGAATCGGGCTCATACCTACTTAGGAAACCCGTCAAAAGAGTCGGAAA
Xanthium (1674) GGCGAATCGGGCTCATACCTACTTAGGAAATCCGTCAAAAGAGTCTGAAA
              1751                                              1800
1248-3  (1745) TATTCCCTAACATGGTGAAGTTTGCTGAAGCCTGTGATATCCCGGCTGCT
  HA89  (1745) TATTCCCTAACATGGTGAAGTTTGCTGAAGCCTGTGATATCCCGGCTGCT
Xanthium (1724) TATTCCCTAACATGTTGAAGTTTGCTGAAGCGTGTGATATCCCAGCTGCC
              1801                                              1850
1248-3  (1795) CGAGTGACCCAAAAGGCGGATCTACGAGCAGCTATTCAGAAGATGTTGGA
  HA89  (1795) CGAGTGACCCAAAAGGCGGATCTACGAGCAGCTATTCAGAAGATGTTGGA
Xanthium (1774) CGAGTGACCCGGAAGGCAGATCTACGAGCAGCTATTCAGAAGATGTTGGA
              1851                                              1900
1248-3  (1845) TACACCCGGGCCTTACTTGTTGGATGTGATTGTGCCGCATCAAGAACACG
  HA89  (1845) TACACCCGGGCCTTACTTGTTGGATGTGATTGTGCCGCATCAAGAACACG
Xanthium (1824) TACACCGGGGCCTTACTTGTTGGATGTGATCGTGCCCCATCAAGAACATG
              1901                                              1950
1248-3  (1895) TGTTGCCCATGATCCCGGCTGGCGGAGGTTTCTCGGATGTGATCACCGAG
  HA89  (1895) TGTTGCCCATGATCCCGGCTGGCGGAGGTTTCTCGGATGTGATCACCGAG
Xanthium (1874) TGTTGCCCATGATCCCGGCTGGTGGAGGTTTCATGGATGTGATCACCGAA
              1951              Stop
1248-3  (1945) GGTGATGGCAGAACGAAATATTGA
  HA89  (1945) GGTGATGGCAGAACGAAATATTGA
Xanthium (1924) GGCGACGGCAGAATGAAATATTGA
```

FIGURE 2

```
                      1                                                50
1248-3      (1)   MAAPP--NPSISFKPPSPAAALPPRSAFLPRFALPITSTTQKRHRLHISN
HA89        (1)   MAAPP--NPSISFKPPSPAAALPPRSAFLPRFALPITSTTQKRHRLHISN
Xanthium    (1)   MAAIPHTNPSITTKPPS----SPPRPTFLARETFPITSTSHKRHRLHISN
                     51                                               100
1248-3     (49)   VLSDSKSTTTTTTTTQRPLPVQPFVSRYAPDQPRKGADVLVEALEREGVT
HA89       (49)   VLSDSKSTTTTTTTTQRPLPVQPFVSRYAPDQPRKGADVLVEALEREGVT
Xanthium   (47)   VLSDSKP-----TITHSPLPTKSFISRYAPDQPRKGADVLVEALEREGVT
                    101                                               150
1248-3     (99)   DVFAYPGGASMEIHQALTRSSTIRNVLPRHEQGGVFAAEGYARASGLPGV
HA89       (99)   DVFAYPGGASMEIHQALTRSSTIRNVLPRHEQGGVFAAEGYARASGLPGV
Xanthium   (92)   DVFAYPGGASMEIHQALTRSTTIRNVLPRHEQGGVFAAEGYARASGLPGV
                                             cd182 (Pro→Leu)
                    151                       *                       200
1248-3    (149)   CIATSGPGATNLVSGLADALLDSVPMVAITGQVLRRMIGTDAFQETPIVE
HA89      (149)   CIATSGPGATNLVSGLADALLDSVPMVAITGQVPRRMIGTDAFQETPIVE
Xanthium  (142)   CIATSGPGATNLVSGLADALLDSVPMVAITGQVPRRMIGTDAFQETPIVE
                    201                                               250
1248-3    (199)   VTRSITKHNYLVLDVEDIPRIVREAFYLASSGRPGPVLIDVPKDIQQQLV
HA89      (199)   VTRSITKHNYLVLDVEDIPRIVREAFYLASSGRPGPVLIDVPKDIQQQLV
Xanthium  (192)   VTRSITKHNYLVLDVEDIPRIVREAFYLASSGRPGPVLIDVPKDIQQQLV
                    251                                               300
1248-3    (249)   VPKWDEPMRLPGYLSRMPKPQYDGHLEQIVRLVGEAKRPVLYVGGGCLNS
HA89      (249)   VPKWDEPMRLPGYLSRMPKPQYDGHLEQIVRLVGEAKRPVLYVGGGCLNS
Xanthium  (242)   VPKWDEPIRLPGYLSRFPKTENNGQLEQIVRLVSEAKRPVLYVGGGCLNS
                    301                                               350
1248-3    (299)   DDELRRFVELTGIPVASTLMGLGAYPASSDLSLHMLGMHGTVYANYAVDK
HA89      (299)   DDELRRFVELTGIPVASTLMGLGAYPASSDLSLHMLGMHGTVYANYAVDK
Xanthium  (292)   GDELRRFVELTGIPVASTLMGLGAYPASSDLSLHMLGMHGTVYANYAVDK
                    351                                               400
1248-3    (349)   SDLLLAFGVRFDDRVTGKLEAFASRAKIVHIDIDPAEIGKNKQPHVSICG
HA89      (349)   SDLLLAFGVRFDDRVTGKLEAFASRAKIVHIDIDPAEIGKNKQPHVSICG
Xanthium  (342)   SDLLLAFGVRFDDRVTGKLEAFASRAKIVHIDIDSAEIGKNKQPHVSICG
                    401                                               450
1248-3    (399)   DIKVALQGLNKILEEKNSVTNLDFSTWRKELDEQKMKFPLSFKTFGEAIP
HA89      (399)   DIKVALQGLNKILEEKNSVTNLDFSTWRKELDEQKMKFPLSFKTFGEAIP
Xanthium  (392)   DIKVALQGLNKILEVKNSVTNLDFSNWRKELDEQKVKYPLSFKTFGEAIP
                    451                                               500
1248-3    (449)   PQYAIQVLDELTGGNAIISTGVGQHQMWAAQFYKYNKPRQWLTSGGLGAM
HA89      (449)   PQYAIQVLDELTGGNAIISTGVGQHQMWAAQFYKYNKPRQWLTSGGLGAM
Xanthium  (442)   PQYAIQVLDELTGGNAIISTGVGQHQMWAAQFYKYNKPRQWLTSGGLGAM
```

FIGURE 2

```
              501                                                      550
   1248-3   (499) GFGLPAAIGAAVARPDAVVVDIDGDGSFMMNVQELATIRVENLPVKILLL
     HA89   (499) GFGLPAAIGAAVARPDAVVVDIDGDGSFMMNVQELATIRVENLPVKILLL
 Xanthium   (492) GFGLPAAIGAAVARPDAVVVDIDGDGSFIMNVQELATIRVENLPVKILLL
              551                                                      600
   1248-3   (549) NNQHLGMVVQWEDRFYKANRAHTYLGNPSKESEIFPNMVKFAEACDIPAA
     HA89   (549) NNQHLGMVVQWEDRFYKANRAHTYLGNPSKESEIFPNMVKFAEACDIPAA
 Xanthium   (542) NNQHLGMVVQWEDRFYKANRAHTYLGNPSKESEIFPNMLKFAEACDIPAA
              601                                                      650
   1248-3   (599) RVTQKADLRAAIQKMLDTPGPYLLDVIVPHQEHVLPMIPAGGGFSDVITE
     HA89   (599) RVTQKADLRAAIQKMLDTPGPYLLDVIVPHQEHVLPMIPAGGGFSDVITE
 Xanthium   (592) RVTRKADLRAAIQKMLDTPGPYLLDVIVPHQEHVLPMIPAGGGFMDVITE
              651
   1248-3   (649) GDGRTKY-
     HA89   (649) GDGRTKY-
 Xanthium   (642) GDGRMKY-
```

HERBICIDE-RESISTANT SUNFLOWER PLANTS, POLYNUCLEOTIDES ENCODING HERBICIDE-RESISTANT ACETOHYDROXYACID SYNTHASE LARGE SUBUNIT PROTEINS, AND METHODS OF USE

FIELD OF THE INVENTION

This invention relates to the field of agricultural biotechnology, particularly to herbicide-resistant sunflower plants and novel polynucleotide sequences that encode wild-type and imidazolinone-resistant sunflower acetohydroxyacid synthase large subunit proteins.

BACKGROUND OF THE INVENTION

Acetohydroxyacid synthase (AHAS; EC 4.1.3.18, also known as acetolactate synthase or ALS), is the first enzyme that catalyzes the biochemical synthesis of the branched chain amino acids valine, leucine and isoleucine (Singh (1999) "Biosynthesis of valine, leucine and isoleucine," in *Plant Amino Acid*, Singh, B. K., ed., Marcel Dekker Inc. New York, N.Y., pp. 227-247). AHAS is the site of action of five structurally diverse herbicide families including the sulfonylureas (Tan et al. (2005) *Pest Manag. Sci.* 61:246-57; Mallory-Smith and Retzinger (2003) *Weed Technology* 17:620-626; 'LaRossa and Falco (1984) *Trends Biotechnol.* 2:158-161), the imidazolinones (Shaner et al. (1984) *Plant Physiol.* 76:545-546), the triazolopyrimidines (Subramanian and Gerwick (1989) "Inhibition of acetolactate synthase by triazolopyrimidines," in *Biocatalysis in Agricultural Biotechnology*, Whitaker, J. R. and Sonnet, P. E. eds., ACS Symposium Series, American Chemical Society, Washington, D.C., pp. 277-288), t Tan et al. (2005) *Pest Manag. Sci.* 61:246-57; Mallory-Smith and Retzinger (2003) *Weed Technology* 17:620-626, the sulfonylamino-carbonyltriazolinones (Tan et al. (2005) *Pest Manag. Sci.* 61:246-57; Mallory-Smith and Retzinger (2003) *Weed Technology* 17:620-626). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulmuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray a herbicide over the top of a wide range of vegetation decreases the costs associated with plantation establishment and maintenance, and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone-resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson (1985) *Weed Sci.* 33:469-471). Other crops such as corn (Newhouse et al. (1992) *Plant Physiol.* 100:882886) and rice (Barrett et al. (1989) *Crop Safeners for Herbicides*, Academic Press, New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al. (1984) *Plant Physiol.* 76:545-546; Brown et al., (1987) *Pestic. Biochem. Physiol.* 27:24-29). Other plant physiological differences such as absorption and translocation also play an important role in sensitivity (Shaner and Robinson (1985) *Weed Sci.* 33:469-471).

Plants resistant to imidazolinones, sulfonylureas and triazolopyrimidines have been successfully produced using seed, microspore, pollen, and callus mutagenesis in *Zea mays, Arabidopsis thaliana, Brassica napus* (i e., canola) *Glycine max, Nicotiana tabacum*, and *Oryza sativa* (Sebastian et al. (1989) *Crop Sci.* 29:1403-1408; Swanson et al., 1989 *Theor. Appl. Genet.* 78:525-530; Newhouse et al. (1991) *Theor. Appl. Genet.* 83:65-70; Sathasivan et al. (1991) *Plant Physiol.* 97:1044-1050; Mourand et al. (1993) *J. Heredity* 84:91-96; U.S. Pat. No. 5,545,822). In all cases, a single, partially dominant nuclear gene conferred resistance. Four imidazolinone resistant wheat plants were also previously isolated following seed mutagenesis of *Triticum aestivum* L. cv. Fidel (Newhouse et al. (1992) *Plant Physiol.* 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al. (1992) *Plant Physiol.* 100:882-886).

Naturally occurring plant populations that were discovered to be resistant to imidazolinone and/or sulfonylurea herbicides have also been used to develop herbicide-resistant sunflower breeding lines. Recently, two sunflower lines that are resistant to a sulfonylurea herbicide were developed using germplasm originating from a wild population of common sunflower (*Helianthus annuus*) as the source of the herbicide-resistance trait (Miller and Al-Khatib (2004) *Crop Sci.* 44:1037-1038). Previously, White et al. ((2002) *Weed Sci.* 50:432-437) had reported that individuals from a wild population of common sunflower from South Dakota, U.S.A. were cross-resistant to an imidazolinone and a sulfonylurea herbicide. Analysis of a portion of the coding region of the acetohydroxyacid synthase large subunit (AHASL) genes of individuals from this population revealed a point mutation that results in an Ala-to-Val amino acid substitution in the sunflower AHASL protein that corresponds to $Ala_{205}$ in the wild-type *Arabidopsis thaliana* AHASL protein (White et al. (2003) *Weed Sci.* 51:845-853).

Computer-based modeling of the three dimensional conformation of the AHAS-inhibitor complex predicts several amino acids in the proposed inhibitor binding pocket as sites where induced mutations would likely confer selective resistance to imidazolinones (Ott et al. (1996) *J. Mol. Biol.* 263:359-368). Wheat plants produced with some of these rationally designed mutations in the proposed binding sites of the AHAS enzyme have in fact exhibited specific resistance to a single class of herbicides (Ott et al. (1996) *J. Mol. Biol.* 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance due to mutations in at least one amino acid in one or more conserved regions. The mutations described therein encode either cross-resistance for imidazolinones and sulfonylureas or sulfonylurea-specific resistance, but imidazolinone-specific resistance is not described. U.S. Pat. No. 5,731,180 and U.S. Pat. No. 5,767,361 discuss an isolated gene having a single amino acid substitution in a wild-type monocot AHAS amino acid sequence that results in imidazolinone-specific resistance. In addition, rice plants that are resistant to herbicides that interfere with AHAS have been developed by mutation breeding and also by the selection of herbicide resistant plants from a pool of rice plants produced by anther culture. See, U.S. Pat. Nos. 5,545,822, 5,736,629, 5,773,703, 5,773,704, 5,952,553 and 6,274,796.

In plants, as in all other organisms examined, the AHAS enzyme is comprised of two subunits: a large subunit (catalytic role) and a small subunit (regulatory role) (Duggleby and Pang (2000) *J. Biochem. Mol. Biol.* 33:1-36). The AHAS large subunit (also referred to herein as AHASL) may be encoded by a single gene as in the case of *Arabidopsis* and rice or by multiple gene family members as in maize, canola, and cotton. Specific, single-nucleotide substitutions in the large subunit confer upon the enzyme a degree of insensitivity to one or more classes of herbicides (Chang and Duggleby (1998) *Biochem J.* 333:765-777).

For example, bread wheat, *Triticum aestivum* L., contains three homoeologous acetohydroxyacid synthase large subunit genes. Each of the genes exhibit significant expression based on herbicide response and biochemical data from mutants in each of the three genes (Ascenzi et al. (2003) International Society of Plant Molecular Biologists Congress, Barcelona, Spain, Ref. No. S10-17). The coding sequences of all three genes share extensive homology at the nucleotide level (WO 03/014357). Through sequencing the AHASL genes from several varieties of *Triticum aestivum*, the molecular basis of herbicide tolerance in most IMI-tolerant (imidazolinone-tolerant) lines was found to be the mutation S653(At)N, indicating a serine to asparagine substitution at a position equivalent to the serine at amino acid 653 in *Arabidopsis thaliana* (WO 03/01436; WO 03/014357). This mutation is due to a single nucleotide polymorphism (SNP) in the DNA sequence encoding the AHASL protein.

Given their high effectiveness and low-toxicity, imidazolinone herbicides are favored for agricultural use. However, the ability to use imidazolinone herbicides in a particular crop production system depends upon the availability of imidazolinone-resistant varieties of the crop plant of interest. To produce such imidazolinone-resistant varieties, plant breeders need to develop breeding lines with the imidazolinone-resistance trait. Thus, additional imidazolinone-resistant breeding lines and varieties of crop plants, as well as methods and compositions for the production and use of imidazolinone-resistant breeding lines and varieties, are needed.

SUMMARY OF THE INVENTION

The present invention provides sunflower plants having increased resistance to herbicides when compared to a wild-type sunflower plant. In particular, the sunflower plants of the invention have increased resistance to at least one herbicide that interferes with the activity of the AHAS enzyme when compared to a wild-type sunflower plant. The herbicide resistant sunflower plants of the invention comprise at least one copy of a gene or polynucleotide that encodes a herbicide-resistant acetohydroxyacid synthase large subunit 1 (AHASL1). Such a herbicide-resistant AHASL1 protein comprises a leucine, alanine, threonine, histidine, arginine, or isoleucine at amino acid position 182 or equivalent position. The herbicide-resistant sunflower plant of the invention can contain one, two, three, four, or more copies of a gene or polynucleotide encoding a herbicide-resistant AHASL1 protein of the invention. The sunflower plants of the invention also include seeds and progeny plants that comprise at least one copy of a gene or polynucleotide encoding a herbicide-resistant AHASL1 protein of the invention.

In one embodiment, the present invention provides herbicide-resistant sunflower plants that are from the sunflower line that has been designated as MUT28. A sample of seeds of the MUT28 line has been deposited with the American Type Culture Collection (ATCC) as ATCC Patent Deposit No. PTA-6084. Such MUT28 sunflower plants comprise in their genomes an AHASL1 gene that comprises the nucleotide sequence set forth in SEQ ID NO: 1 and that encodes the AHASL1 protein comprising, the amino acid sequence set forth in SEQ ID NO: 2. When compared to the amino acid sequence of the AHASL1 protein (SEQ ID NO: 4) that is encoded by an AHASL1 gene (SEQ ID NO: 3) from a wild-type sunflower plant, the amino acid sequence set forth in SEQ ID NO: 2 has a single amino acid difference from the wild-type amino acid sequence. In the amino acid sequence set forth in SEQ ID NO: 2, there is a leucine at amino acid position 182. In the wild-type amino acid sequence set forth in SEQ ID NO: 4, this same amino acid position has a proline.

The present invention further provides isolated polynucleotides and isolated polypeptides for sunflower (*Helianthus annuus*) AHASL1 proteins. The polynucleotides of the invention encompass nucleotide sequences that encode herbicide-resistant and wild-type AHASL1 proteins. The herbicide-resistant AHASL1 proteins of the invention are herbicide-resistant AHASL1 proteins that possess a proline-to-leucine substitution at position 182 in their respective amino acid sequences, when compared to the corresponding wild-type amino acid sequence. The polynucleotides of the invention encompass the nucleotide sequences set forth in SEQ ID NOS: 1 and 3, nucleotide sequences encoding the amino acid sequences set forth in SEQ ID NOS: 2 and 4, and fragments and variants of said nucleotide sequences that encode proteins comprising AHAS activity. The polynucleotides of the invention further encompass nucleotide sequences that encode mature forms of the AHASL1 proteins described above particularly the nucleotides sequences SEQ ID NOS: 5 and 7, nucleotide sequences encoding the amino acid sequences set forth in SEQ ID NOS: 6 and 8, and fragments and variants of said nucleotide sequences that encode proteins comprising AHAS activity. Such mature forms of AHASL1 proteins lack the chloroplast transit peptide that is part of the full-length AHASL1 proteins.

The present invention provides expression cassettes for expressing the polynucleotides of the invention in plants, plant cells, and other, non-human host cells. The expression cassettes comprise a promoter expressible in the plant, plant cell, or other host cells of interest operably linked to a polynucleotide of the invention that encodes either a wild-type or herbicide-resistant AHASL1 protein. If necessary for targeting expression to the chloroplast, the expression cassette can also comprise an operably linked chloroplast-targeting sequence that encodes of a chloroplast transit peptide to direct an expressed AHASL1 protein to the chloroplast. The expression cassettes of the invention find use in a method for enhancing the herbicide tolerance of a plant and a host cell. The method involves transforming the plant or host cell with an expression cassette of the invention, wherein the expression cassette comprises a promoter that is expressible in the plant or host cell of interest and the promoter is operably linked to a polynucleotide of the invention that encodes an herbicide-resistant AHASL1 protein of the invention. The method further comprises regenerating a transformed plant from the transformed plant cell.

The present invention provides a method for increasing AHAS activity in a plant comprising transforming a plant cell with a polynucleotide construct comprising a nucleotide sequence operably linked to a promoter that drives expression in a plant cell and regenerating a transformed plant from the transformed plant cell. The nucleotide sequence is selected from those nucleotide sequences that encode the herbicide-resistant or wild-type AHASL1 proteins of the invention, particularly the nucleotide sequences set forth in SEQ ID NOS: 1, 3, 5, and 7, nucleotide sequences encoding the amino acid sequences set forth in SEQ ID NOS: 2, 4, 6, and 8, and fragments and variants thereof. A plant produced by this method comprises increased AHAS activity, when compared to an untransformed plant.

The present invention provides a method for producing a herbicide-resistant plant comprising transforming a plant cell with a polynucleotide construct comprising a nucleotide sequence operably linked to a promoter that drives expression in a plant cell and regenerating a transformed plant from said transformed plant cell. The nucleotide sequence is selected from those nucleotide sequences that encode the herbicide-resistant AHASL1 proteins of the invention, particularly the nucleotide sequences set forth in SEQ ID NOS: 1 and 5, nucleotide sequences encoding the amino acid sequences set forth in SEQ ID NOS: 2 and 6, and fragments and variants thereof, including, but not limited to, the mature forms of the herbicide-resistant AHASL1 proteins of the invention. A herbicide-resistant plant produced by this method comprises enhanced resistance, compared to an untransformed plant, to at least one herbicide, particularly a herbicide that interferes with the activity of the AHAS enzyme such as, for example, an imidazolinone herbicide or a sulfonylurea herbicide.

The present invention provides a method for enhancing herbicide-tolerance in a herbicide-tolerant plant. The method finds use in enhancing the resistance of a plant that already is resistant to a level of a herbicide that would kill or significantly injure a wild-type plant. Such a herbicide-tolerant plant can be a herbicide-tolerant plant that has been genetically engineered for herbicide-tolerance or a herbicide-tolerant plant that was developed by means that do not involve recombinant DNA such as, for example, the MUT28 sunflower plants of the present invention. The method comprises transforming a herbicide-tolerant plant with a polynucleotide construct comprising a nucleotide sequence operably linked to a promoter that drives expression in a plant cell and regenerating a transformed plant from the transformed plant cell. The nucleotide sequence is selected from those nucleotide sequences that encode the herbicide-resistant AHASL1 proteins of the invention, particularly the nucleotide sequences set forth in SEQ ID NO: 1 and 5, nucleotide sequences encoding the amino acid sequences set forth in SEQ ID NO: 2 and 6, and fragments and variants thereof.

The present invention provides transformation vectors comprising a selectable marker gene of the invention. The selectable marker gene comprises a promoter that drives expression in a host cell operably linked to a polynucleotide comprising a nucleotide sequence that encodes an herbicide-resistant AHASL1 protein of the invention. The transformation vector can additionally comprise a gene of interest to be expressed in the host cell and can also, if desired, include a chloroplast-targeting sequence that is operably linked to the polynucleotide of the invention.

The present invention further provides methods for using the transformation vectors of the invention to select for cells transformed with the gene of interest. Such methods involve the transformation of a host cell with the transformation vector, exposing the cell to a level of an imidazolinone or sulfonylurea herbicide that would kill or inhibit the growth of a non-transformed host cell, and identifying the transformed host cell by its ability to grow in the presence of the herbicide. In one embodiment of the invention, the host cell is a plant cell and the selectable marker gene comprises a promoter that drives expression in a plant cell.

The present invention provides a method for controlling weeds in the vicinity of the herbicide-resistant plants of the invention, including the herbicide-resistant sunflower plants described above and plants transformed with the herbicide-resistant AHASL1 polynucleotides of the invention. Such transformed plants comprise in their genomes at least one expression cassette comprising a promoter that drives gene expression in a plant cell, wherein the promoter is operably linked to an AHASL1 polynucleotide of the invention. The method comprises applying an effective amount of an herbicide to the weeds and to the herbicide-resistant plant, wherein the herbicide-resistant plant, plant has increased resistance to at least one herbicide, particularly an imidazolinone or sulfonylurea herbicide, when compared to a wild-type or untransformed plant.

The plants of the present invention can be transgenic or non-transgenic. An example of a non-transgenic sunflower plant having increased resistance to imidazolinone and/or sulfonylurea herbicides includes the sunflower plant (MUT28) having ATCC Patent Deposit No. PTA-6084; or mutant, recombinant, or a genetically engineered derivative of the plant having ATCC Patent Deposit No. PTA-6084; or of any progeny of the plant having ATCC Patent Deposit No. PTA-6084; or a plant that is a progeny of any of these plants; or a plant that comprises the herbicide resistance characteristics of the plant having ATCC Patent Deposit No. PTA-6084.

The present invention also provides plants, plant organs, plant tissues, plant cells, seeds, and non-human host cells that are transformed with the at least one polynucleotide, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

The present invention further provides isolated polypeptides comprising imidazolinone-resistant and wild-type sunflower AHASL1 proteins. The isolated polypeptides comprise the amino acid sequences set forth in SEQ ID NOS: 2 and 4, the amino acid sequences encoded by nucleotide sequences set forth in SEQ ID NOS: 1 and 3, and fragments and variants of said amino acid sequences that encode proteins comprising AHAS activity, including, but not limited to, the mature forms of the AHASL1 proteins of the invention that are set forth in SEQ ID NOS: 6 and 8 and those encoded by the nucleotide sequences set forth in SEQ ID NOS: 5 and 7.

BRIEF DESCRIPTION THE DRAWINGS

FIG. 1 is a nucleotide sequence alignment of the complete coding sequences of the herbicide-resistant sunflower AHASL1 gene (SEQ ID NO: 1), the wild-type sunflower AHASL1 gene. (SEQ ID NO: 3) and a herbicide-resistant AHASL1 gene from *Xanthium* sp. (SEQ ID NO: 9, GenBank Accession No. U16280). In the figure, 1248-3, HA89, and *Xanthium* refer to SEQ ID NOS: 1, 3, and 9, respectively. The asterisk indicates the site of the single mutation found in the herbicide-resistant sunflower AHASL1 coding sequence. The mutation is a C-to-T transition in nucleotide 545 (codon 182) of SEQ ID NO: 1. Light-shaded regions indicate that the nucleotide at that position is conserved across the three aligned sequences. Dark-shaded regions indicate that the nucleotide at that position is conserved in two of the three sequences.

FIG. 2 is an amino acid sequence alignment of the herbicide-resistant sunflower AHASL1 protein (SEQ ID NO: 2), the wild-type sunflower AHASL1 protein (SEQ ID NO: 4) and a herbicide-resistant AHASL1 protein from *Xanthium* sp. (SEQ ID NO: 10, GenBank Accession No. U16280). In the figure, 1248-3, HA89, and *Xanthium* refer to SEQ ID NOS: 2, 4, and 10, respectively. The asterisk indicates the site of the single amino acid substitution found in the herbicide-resistant sunflower AHASL1 protein. In the herbicide resistant protein (SEQ ID NO: 2) the proline at amino acid number 182 of the wild-type protein (SEQ ID NO: 4) is substituted with a leucine. Light-shaded regions indicate that the amino acid at that position is conserved across the three aligned sequences. Dark-shaded regions indicate that the amino acid at that position is conserved in two of the three sequences. Amino acids represented by bold-face type indicate conservative amino acid substitutions.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth the nucleotide sequence encoding the herbicide-resistant AHASL1 protein from sunflower. By comparison to GenBank Accession No. U16280, the mature form of the AHASL1 protein is encoded by the nucleotide sequence corresponds to nucleotides 253 to 1965 of SEQ ID NO: 1, and the transit peptide is encoded by nucleotides 1 to 252.

SEQ ID NO: 2 sets forth the amino acid sequence of the herbicide-resistant AHASL1 protein from sunflower. By comparison to GenBank Accession No. U16280, the amino acid sequence of the mature form of the AHASL1 protein corresponds to amino acids 85 to 655 of SEQ ID NO: 2, and the transit peptide corresponds to amino acids 1 to 84.

SEQ ID NO: 3 sets forth the nucleotide sequence encoding the AHASL1 protein from sunflower. By comparison to GenBank Accession No. U16280, the mature form of the AHASL1 protein is encoded by the nucleotide sequence corresponds to nucleotides 253 to 1965 of SEQ ID NO: 3, and the transit peptide is encoded by nucleotides 1 to 252.

SEQ ID NO: 4 sets forth the amino acid sequence of the AHASL1 protein from sunflower. By comparison to GenBank Accession No. U16280, the amino acid sequence of the mature form of the AHASL1 protein corresponds to amino acids 85 to 655 of SEQ ID NO: 4, and the transit peptide corresponds to amino acids 1 to 84.

SEQ ID NO: 5 sets forth the nucleotide sequence encoding the mature, herbicide-resistant AHASL1 protein from sunflower. This nucleotide sequence corresponds to nucleotides 253 to 1965 of SEQ ID NO: 1.

SEQ ID NO: 6 sets forth the amino acid sequence of the mature, herbicide-resistant AHASL1 protein from sunflower. This amino acid sequence corresponds to amino acids 85 to 655 of SEQ ID NO: 2.

SEQ ID NO: 7 sets forth the nucleotide sequence encoding the mature AHASL1 protein from sunflower. This nucleotide sequence corresponds to nucleotides 253 to 1965 of SEQ ID NO: 3.

SEQ ID NO: 8 sets forth the amino acid sequence of the mature AHASL1 protein from sunflower. This amino acid sequence corresponds to amino acids 85 to 655 of SEQ ID NO: 4.

SEQ ID NO: 9 sets forth the nucleotide sequence of GenBank Accession No. U16280.

SEQ ID NO: 10 sets forth the amino acid sequence of GenBank Accession No. U16280.

SEQ ID NO: 11 sets forth the nucleotide sequence of the ALS1-1F primer that is described in Example 2.

SEQ ID NO: 12 sets forth the nucleotide sequence of the ALS1-1R primer that is described in Example 2.

SEQ ID NO: 13 sets forth the nucleotide sequence of the ALS1-2F primer that is described in Example 2.

SEQ ID NO: 14 sets forth the nucleotide sequence of the ALS1-2R primer that is described in Example 2.

SEQ ID NO: 15 sets forth the nucleotide sequence of the ALS1-3F primer that is described in Example 2.

SEQ ID NO: 16 sets forth the nucleotide sequence of the ALS1-3R primer that is described in Example 2.

SEQ ID NO: 17 sets forth the nucleotide sequence of the ALS-3F primer that is described in Example 2.

SEQ ID NO: 18 sets forth the nucleotide sequence of the SUNALS1F primer that is described in Example 2.

SEQ ID NO: 19 sets forth the nucleotide sequence of the ALS-6R primer that is described in Example 2.

DETAILED DESCRIPTION OF THE INVENTION

The present invention relates to sunflower plants having increased resistance to herbicides when compared to a wild-type sunflower plant. Herbicide resistant sunflower plants were produced as described hereinbelow by exposing wild-type (with respect to herbicide resistance) sunflower plants to a mutagen, allowing the plants to mature and reproduce, and selecting progeny plants that displayed enhanced resistance to an imidazolinone herbicide, relative to the resistance of a wild-type sunflower plant. The invention provides a herbicide resistant sunflower line that is referred to herein as MUT28.

From the MUT28 herbicide-resistant sunflower plants and wild-type sunflower plants, the coding region of an acetohydroxyacid synthase large subunit gene (designated as AHASL1) was isolated by polymerase chain reaction (PCR)

amplification and sequenced. By comparing the polynucleotide sequences of the herbicide resistant and wild-type sunflower plants, it was discovered that the coding region of the AHASL1 polynucleotide sequence from the herbicide resistant sunflower plant differed from the AHASL1 polynucleotide sequence of the wild type plant by a single nucleotide, a C-to-T transition at nucleotide 545 (FIG. 1). This C-to-T transition in the AHASL1 polynucleotide sequence results in a Pro-to-Leu substitution at amino acid 182 in a conserved region of the predicted amino acid sequence of the AHASL1 protein, relative to the amino acid sequence of the wild-type AHASL1 protein (FIG. 2). A variety of amino acid substitutions for the proline in this conserved region of the plant AHASL proteins, including the Pro-to-Leu substitution, are known to confer on a plant, which comprises such an AHASL protein, resistance to imidazolinone and/or sulfonylurea herbicides. See, Boutsalis et al. (1999) Pestic. Sci. 55:507-516; Guttieri et al. (1992) Weed Sci. 40:670-678; Guttieri et al. (1995) Weed Sci. 43:143-178; and U.S. Pat. No. 5,141,870; all of which are herein incorporated by reference. See also, Example 3, below.

As used herein, unless indicated otherwise or apparent from the context, the term "plant" includes, but is not limited to, plant cells, plant protoplasts, plant cell tissue cultures from which plants can be regenerated, plant calli, plant clumps, plant cells that are intact in plants, or parts of plants such as, for example, embryos, pollen, ovules, seeds, cotyledons, leaves, stems, flowers, branches, petioles, fruit, roots, root tips, anthers, and the like.

The invention further relates to isolated polynucleotide molecules comprising nucleotide sequences that encode acetohydroxyacid synthase large subunit (AHASL) proteins and to such AHASL proteins. The invention discloses the isolation and nucleotide sequence of a polynucleotide encoding a herbicide-resistant sunflower AHASL1 protein from an herbicide-resistant sunflower plant that was produced by chemical mutagenesis of wild-type sunflower plants. The herbicide-resistant AHASL1 proteins of the invention possess a proline-to-leucine substitution at position 182 in their respective amino acid sequences, when compared to the corresponding wild-type amino acid sequence. The invention further discloses the isolation and nucleotide sequence of a polynucleotide molecule encoding a wild-type sunflower AHASL1 protein.

The present invention provides isolated polynucleotide molecules that encode AHASL1 proteins from sunflower (*Helianthus annuus* L.). Specifically, the invention provides isolated polynucleotide molecules comprising: the nucleotide sequences set forth in SEQ ID NOS: 1 and 3, nucleotide sequences encoding AHASL1 proteins comprising the amino acid sequences set forth in SEQ ID NOS: 2 and 4, and fragments and variants of such nucleotide sequences that encode functional AHASL1 proteins.

In addition, the present invention provides isolated polynucleotides encoding the mature AHASL1 proteins. The mature AHASL1 proteins of the invention lack the chloroplast transit peptide that is found at the N-terminal end of each of the AHASL1 proteins but retain AHAS activity. In particular, the polynucleotides of the invention comprise a nucleotide sequence selected from the group consisting of the nucleotide sequences set forth in SEQ ID NOS: 5 and 7, nucleotide sequences encoding the amino acid sequences set forth in SEQ ID NOS: 6 and 8, and fragments and variants of these nucleotide sequences that encode a mature AHASL1 polypeptide comprising AHAS activity.

The isolated herbicide-resistant AHASL1 polynucleotide molecules of the invention comprise nucleotide sequences that encode herbicide-resistant AHASL1 proteins. Such polynucleotide molecules can be used in polynucleotide constructs for the transformation of plants, particularly crop plants, to enhance the resistance of the plants to herbicides, particularly herbicides that are known to inhibit AHAS activity, more particularly imidazolinone herbicides. Such polynucleotide constructs can be used in expression cassettes, expression vectors, transformation vectors, plasmids and the like. The transgenic plants obtained following transformation with such polynucleotide constructs show increased resistance to AHAS-inhibiting herbicides such as, for example, imidazolinone and sulfonylurea herbicides.

Compositions of the invention include nucleotide sequences that encode AHASL1 proteins. In particular, the present invention provides for isolated polynucleotide molecules comprising nucleotide sequences encoding the amino acid sequences shown in SEQ ID NOS: 2, 4, 6, and 8, and fragments and variants thereof that encode polypeptides comprising AHAS activity. Further provided are polypeptides having an amino acid sequence encoded by a polynucleotide molecule described herein, for example those set forth in SEQ ID NOS: 1, 3, 5, and 7, and fragments and variants thereof that encode polypeptides comprising AHAS activity.

The invention encompasses isolated or substantially purified nucleic acid or protein compositions. An "isolated" or "purified" polynucleotide molecule or protein, or biologically active portion thereof, is substantially or essentially free from components that normally accompany or interact with the polynucleotide molecule or protein as found in its naturally occurring environment. Thus, an isolated or purified polynucleotide molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated polynucleotide molecule can contain less than about 5 kb, 4 kb, 3 kb, 2 kb, 1 kb, 0.5 kb, or 0.1 kb of nucleotide sequences that naturally flank the polynucleotide molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

The present invention provides isolated polypeptides comprising AHASL1 proteins. The isolated polypeptides comprise an amino acid sequence selected from the group consisting of the amino acid sequences set forth in SEQ ID NOS: 2 and 4, the amino acid sequences encoded by nucleotide sequences set forth in SEQ ID NOS: 1 and 3, and functional fragments and variants of said amino acid sequences that encode an AHASL1 polypeptide comprising AHAS activity. By "functional fragments and variants" is intended fragments and variants of the exemplified polypeptides that comprise AHAS activity.

Additionally provided are isolated polypeptides comprising the mature forms of the AHASL1 proteins of the invention. Such isolated polypeptides comprise an amino acid sequence selected from the group consisting of the amino acid sequences set forth in SEQ ID NOS: 6 and 8, the amino acid sequences encoded by the nucleotide sequences set forth in SEQ ID NOS: 5 and 7, and functional fragments and variants of said amino acid sequences that encode polypeptides comprising AHAS activity.

In certain embodiments of the invention, the methods involve the use of herbicide-tolerant or herbicide-resistant plants. By an "herbicide-tolerant" or "herbicide-resistant" plant, it is intended that a plant that is tolerant or resistant to at least one herbicide at a level that would normally kill, or inhibit the growth of, a normal or wild-type plant. In one embodiment of the invention, the herbicide-tolerant plants of the invention comprise a herbicide-tolerant or herbicide-resistant AHASL protein. By "herbicide-tolerant AHASL protein" or "herbicide-resistant AHASL protein", it is intended that such an AHASL protein displays higher AHAS activity, relative to the AHAS activity of a wild-type AHASL protein, when in the presence of at least one herbicide that is known to interfere with AHAS activity and at a concentration or level of the herbicide that is to known to inhibit the AHAS activity of the wild-type AHASL protein. Furthermore, the AHAS activity of such a herbicide-tolerant or herbicide-resistant AHASL protein may be referred to herein as "herbicide-tolerant" or "herbicide-resistant" AHAS activity.

For the present invention, the terms "herbicide-tolerant" and "herbicide-resistant" are used interchangeable and are intended to have an equivalent meaning and an equivalent scope. Similarly, the terms "herbicide-tolerance" and "herbicide-resistance" are used interchangeable and are intended to have an equivalent meaning and an equivalent scope. Likewise, the terms "imidazolinone-resistant" and "imidazolinone-resistance" are used interchangeable and are intended to be of an equivalent meaning and an equivalent scope as the terms "imidazolinone-tolerant" and "imidazolinone-tolerance", respectively.

The invention encompasses herbicide-resistant AHASL1 polynucleotides and herbicide-resistant AHASL1 proteins. By "herbicide-resistant AHASL1 polynucleotide" is intended a polynucleotide that encodes a protein comprising herbicide-resistant AHAS activity. By "herbicide-resistant AHASL1 protein" is intended a protein or polypeptide that comprises herbicide-resistant AHAS activity.

Further, it is recognized that a herbicide-tolerant or herbicide-resistant AHASL protein can be introduced into a plant by transforming a plant or ancestor thereof with a nucleotide sequence encoding a herbicide-tolerant or herbicide-resistant AHASL protein. Such herbicide-tolerant or herbicide-resistant AHASL proteins are encoded by the herbicide-tolerant or herbicide-resistant AHASL polynucleotides. Alternatively, a herbicide-tolerant or herbicide-resistant AHASL protein may occur in a plant as a result of a naturally occurring or induced mutation in an endogenous AHASL gene in the genome of a plant or progenitor thereof.

The present invention provides plants, plant tissues, plant cells, and host cells with increased resistance or tolerance to at least one herbicide, particularly a herbicide that interferes with the activity of the AHAS enzyme, more particularly an imidazolinone or sulfonylurea herbicide. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, or host cell, but that said amount does not kill or inhibit as severely the growth of the herbicide-resistant plants, plant tissues, plant cells, and host cells of the present invention. Typically, the effective amount of a herbicide is an amount that is routinely used in agricultural production systems to kill weeds of interest. Such an amount is known to those of ordinary skill in the art.

The herbicides of the present invention are those that interfere with the activity of the AHAS enzyme such that AHAS activity is reduced in the presence of the herbicide. Such herbicides may also referred to herein as "AHAS-inhibiting herbicides" or simply "AHAS inhibitors." As used herein, an "AHAS-inhibiting herbicide" or an "AHAS inhibitor" is not meant to be limited to single herbicide that interferes with the activity of the AHAS enzyme. Thus, unless otherwise stated or evident from the context, an "AHAS-inhibiting herbicide" or an "AHAS inhibitor" can be a one herbicide or a mixture of two, three, four, or more herbicides, each of which interferes with the activity of the AHAS enzyme.

By "similar, wild-type, plant, plant tissue, plant cell or host cell" is intended a plant, plant tissue, plant cell, or host cell, respectively, that lacks the herbicide-resistance characteristics and/or particular polynucleotide of the invention that are disclosed herein. The use of the term "wild-type" is not, therefore, intended to imply that a plant, plant tissue, plant cell, or other host cell lacks recombinant DNA in its genome, and/or does not possess herbicide resistant characteristics that are different from those disclosed herein.

As used herein unless clearly indicated otherwise, the term "plant" intended to mean a plant any developmental stage, as well as any part or parts of a plant that may be attached to or separate from a whole intact plant. Such parts of a plant include, but are not limited to, organs, tissues, and cells of a plant. Examples of particular plant parts include a stem, a leaf, a root, an inflorescence, a flower, a floret, a fruit, a pedicle, a peduncle, a stamen, an anther, a stigma, a style, an ovary, a petal, a sepal, a carpel, a root tip, a root cap, a root hair, a leaf hair, a seed hair, a pollen grain, a microspore, a cotyledon, a hypocotyl, an epicotyl, xylem, phloem, parenchyma, endosperm, a companion cell, a guard cell, and any other known organs, tissues, and cells of a plant. Furthermore, it is recognized that a seed is a plant.

The plants of the present invention include both non-transgenic plants and transgenic plants. By "non-transgenic plant" is intended mean a plant lacking recombinant DNA in its genome. By "transgenic plant" is intended to mean a plant comprising recombinant DNA in its genome. Such a transgenic plant can be produced by introducing recombinant DNA into the genome of the plant. When such recombinant DNA is incorporated into the genome of the transgenic plant, progeny of the plant can also comprise the recombinant DNA. A progeny plant that comprises at least a portion of the recombinant DNA of at least one progenitor transgenic plant is also a transgenic plant.

The present invention provides the herbicide-resistant sunflower line that is referred to herein as MUT28. A deposit of at least 650 seeds from sunflower line MUT28 with the Patent Depository of the American Type Culture Collection (ATCC), Mansassas, Va. 20110 USA was made on Jun. 18, 2004 and assigned ATCC Patent Deposit Number PTA-6084. On Jul. 15, 2005, additional seeds of the MUT28 line were deposited with the ATCC to reach a total of more than 2500 seeds for ATCC Patent Deposit Number PTA-6084. The deposit will be maintained under the terms of the Budapest Treaty on the International Recognition of the Deposit of Microorganisms for the Purposes of Patent Procedure. The deposit of sunflower line MUT28 was made for a term of at least 30 years and at least 5 years after the most recent request for the furnishing of a sample of the deposit is received by the ATCC. Additionally, Applicants have satisfied all the requirements of 37 C.F.R. §§1.801-1.809, including providing an indication of the viability of the sample.

The present invention provides herbicide-resistant sunflower plants of the MUT28 line that were produced by a mutation breeding. Wild-type sunflower plants were mutagenized by exposing the plants to a mutagen, particularly a chemical mutagen, more particularly ethyl methanesulfonate (EMS). However, the present invention is not limited to herbicide-resistant sunflower plants that are produced by a mutagensis method involving the chemical mutagen EMS. Any mutagensis method known in the art may be used to produce the herbicide-resistant sunflower plants of the present invention. Such mutagensis methods can involve, for example, the use of any one or more of the following mutagens: radiation, such as X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation (preferably from 2500 to 2900 nm), and chemical mutagens such as base analogues (e.g., 5-bromo-uracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Herbicide-resistant plants can also be produced by using tissue culture methods to select for plant cells comprising herbicide-resistance mutations and then regenerating herbicide-resistant plants therefrom. See, for example, U.S. Pat. Nos. 5,773,702 and 5,859,348, both of which are herein incorporated in their entirety by reference. Further details of mutation breeding can be found in "Principals of Cultivar Development" Fehr, 1993 Macmillan Publishing Company the disclosure of which is incorporated herein by reference.

Analysis of the AHASL1 gene of the sunflower plant of the MUT28 line revealed that mutation that results in the substitution of a leucine for the proline that is found at amino acid position 182 in the wild-type AHASL1 amino acid sequence for SEQ ID NO: 4. Thus, the present invention discloses that substituting another amino acid for the proline at position 182 can cause a sunflower plant to have enhanced resistance to a herbicide, particularly an imidazolinone and/or sulfonylurea herbicide. As disclosed in Example 3 below, proline 182 is found in a conserved region of AHASL proteins and other amino acid substitutions have been disclosed that are known to confer herbicide resistance on a plant that comprises such an AHASL protein. Accordingly, the herbicide-resistant sunflower plants of the invention include, but are not limited to those sunflower plants which comprise in their genomes at least one copy of an AHASL1 polynucleotide that encodes a herbicide-resistant AHASL1 protein that comprises a leucine, alanine, threonine, histidine, arginine, or isoleucine at amino acid position 182 or equivalent position.

The sunflower plants of the invention further include plants that comprise, relative to the wild-type AHASL1 protein, a leucine, alanine, threonine, histidine, arginine, or isoleucine at amino acid position 182 or equivalent position and one or more additional amino acid substitutions in the AHASL1 protein relative to the wild-type AHASL1 protein, wherein such a sunflower plant has increased resistance to at least one herbicide when compared to a wild-type sunflower plant. Such sunflower plants comprise AHASL1 proteins that comprise at least one member selected from the group consisting of: a threonine at amino acid position 107 or equivalent position; an aspartate or valine at amino acid position 190 or equivalent position; a leucine at amino acid position 559 or equivalent position; and an asparagine, threonine, phenylalanine, or valine at amino acid position 638 or equivalent position.

The present invention provides AHASL1 proteins with amino acid substitutions at particular amino acid positions within conserved regions of the sunflower AHASL1 proteins disclosed herein. Unless otherwise indicated herein, particular amino acid positions refer to the position of that amino acid in the fall-length sunflower AHASL1 amino acid sequences set forth in SEQ ID NOS: 2 and 4. Furthermore, those of ordinary skill will recognize that such amino acid positions can vary depending on whether amino acids are added or removed from, for example, the N-terminal end of an amino acid sequence. Thus, the invention encompasses the amino substitutions at the recited position or equivalent position (e.g., "amino acid position 182 or equivalent position"). By "equivalent position" is intended to mean a position that is within the same conserved region as the exemplified amino acid position. For example, the equivalent position in SEQ ID NO: 8 is amino acid 98 for the proline that occurs at amino acid position 182 in SEQ ID NO: 4.

In addition, the present invention provides AHASL1 polypeptides comprising amino acid substitutions that are known to confer resistance on a plant to at least one herbicide, particularly an AHAS-inhibiting herbicide, more particularly an imidazolinone herbicide and/or a sulfonylurea herbicide. Such AHASL1 polypeptides include, for example, those that comprise at least one member selected from the group consisting of: a leucine, alanine, threonine, histidine, arginine, or isoleucine at amino acid position 182 or equivalent position; a threonine at amino acid position 107 or equivalent position; an aspartate or valine at amino acid position 190 or equivalent position; a leucine at amino acid position 559 or equivalent position; and an asparagine, threonine, phenylalanine, or valine at amino acid position 638 or equivalent position. The invention further provides isolated polynucleotides encoding such AHASL1 polypeptides, as well as expression cassettes, transformation vectors, transformed host cells, transformed plants, and methods comprising such polynucleotides.

The present invention provides methods for enhancing the tolerance or resistance of a plant, plant tissue, plant cell, or other host cell to at least one herbicide that interferes with the activity of the AHAS enzyme. Preferably, such an AHAS-inhibiting herbicide is an imidazolinone herbicide, a sulfonylurea herbicide, a triazolopyrimidine herbicide, a pyrimidinyloxybenzoate herbicide, a sulfonylamino-carbonyltriazolinone herbicide, or mixture thereof. More preferably, such a herbicide is an imidazolinone herbicide, a sulfonylurea herbicide, or mixture thereof. For the present invention, the imidazolinone herbicides include, but are not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, and a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidiazolin-2-yl)-nicotinic acid 2-(4-isopropyl-4-methyl-5-oxo-2-imidazolin-2-yl)-3-quinolinecarboxylic acid 5-ethyl-2-(4-isopropl-yl-4-methyl-5-oxo-2-imidazolin-2-y1)-nicotinic acid 2-(4-isopropyl-4-methyl-5-oxo-2-imidazolin-2-yl)-5-methoxymethyl)-nicotinic acid, 2-(4-isopropyl-4-methyl-5-oxo-2-imidazolin-2-yl)-5-methylnicotinic acid and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5- (methoxymethyl)-nicotinic acid is particularly preferred.

For the present invention, the sulfonylurea herbicides include, but are not limited to, chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfiuon, fluzasulfuron, imazosulfuron, pyrazosulfuron ethyl, halosulfuron, azimsulfuron, cyclosulfuron, ethoxysulfuron, flazasulfuron, flupyrsulfuron methyl, foramsulfuron, iodosulfuron, oxasulfuron, mesosulfuron, prosulfuron, sulfosulfuron, trifloxysulfuron, tritosulfuron, a derivative of any of the aforementioned herbicides, and a mixture of two or more of the aforementioned herbicides. The triazolopyrimidine herbicides of the invention include, but are not limited to, cloransulam, diclosulam, florasulam, flumetsulam, metosulam, and penoxsulam. The pyrimidinyloxybenzoate herbicides of the invention include, but are not limited to, bispyribac, pyrithiobac, pyriminobac, pyribenzoxim and pyriftalid. The sulfonylamino-carbonyltriazolinone herbicides include, but are not limited to, flucarbazone and propoxycarbazone.

It is recognized that pyrimidinyloxybenzoate herbicides are closely related to the pyrimidinylthiobenzoate herbicides and are generalized under the heading of the latter name by the Weed Science Society of America Accordingly, the herbicides of the present invention further include pyrimidinylthiobenzoate herbicides, including, but not limited to, the pyrimidinyloxybenzoate herbicides described above.

The present invention provides methods for enhancing AHAS activity in a plant comprising transforming a plant with a polynucleotide construct comprising a promoter operably linked to an AHASL1 nucleotide sequence of the invention. The methods involve introducing a polynucleotide construct of the invention into at least one plant cell and regenerating a transformed plant therefrom. The methods involve the use of a promoter that is capable of driving gene expression in a plant cell. Preferably, such a promoter is a constitutive promoter or a tissue-preferred promoter. The methods find use in enhancing or increasing the resistance of a plant to at least one herbicide that interferes with the catalytic activity of the AHAS enzyme, particularly an imidazolinone herbicide.

The present invention provides expression cassettes for expressing the polynucleotides of the invention in plants, plant tissues, plant cells, and other host cells. The expression cassettes comprise a promoter expressible in the plant, plant tissue, plant cell, or other host cells of interest operably linked to a polynucleotide of the invention that comprises a nucleotide sequence encoding either a full-length (i.e. including the chloroplast transit peptide) or mature AHASL1 protein (i.e. without the chloroplast transit peptide). If expression is desired in the plastids or chloroplasts of plants or plant cells, the expression cassette may also comprise an operably linked chloroplast-targeting sequence that encodes a chloroplast transit peptide.

The expression cassettes of the invention find use in a method for enhancing the herbicide tolerance of a plant or a host cell. The method involves transforming the plant or host cell with an expression cassette of the invention, wherein the expression cassette comprises a promoter that is expressible in the plant or host cell of interest and the promoter is operably linked to a polynucleotide of the invention that comprises a nucleotide sequence encoding an imidazolinone-resistant AHASL1 protein of the invention.

The use of the term "polynucleotide constructs" herein is not intended to limit the present invention to polynucleotide constructs comprising DNA. Those of ordinary skill in the art will recognize that polynucleotide constructs, particularly polynucleotides and oligonucleotides, comprised of ribonucleotides and combinations of ribonucleotides and deoxyribonucleotides may also be employed in the methods disclosed herein. Thus, the polynucleotide constructs of the present invention encompass all polynucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The polynucleotide constructs of the invention also encompass all forms of polynucleotide constructs including, but not limited to, single-stranded forms, double-stranded forms, hairpins, stem-and-loop structures, and the like. Furthermore, it is understood by those of ordinary skill the art that each nucleotide sequences disclosed herein also encompasses the complement of that exemplified nucleotide sequence.

Furthermore, it is recognized that the methods of the invention may employ a polynucleotide construct that is capable of directing, in a transformed plant, the expression of at least one protein, or at least one RNA, such as, for example, an antisense RNA that is complementary to at least a portion of an mRNA. Typically such a polynucleotide construct is comprised of a coding sequence for a protein or an RNA operably linked to 5' and 3' transcriptional regulatory regions. Alternatively, it is also recognized that the methods of the invention may employ a polynucleotide construct that is not capable of directing, in a transformed plant, the expression of a protein or an RNA.

Further, it is recognized that, for expression of a polynucleotides of the invention in a host cell of interest, the polynucleotide is typically operably linked to a promoter that is capable of driving gene expression in the host cell of interest. The methods of the invention for expressing the polynucleotides in host cells do not depend on particular promoter. The methods encompass the use of any promoter that is known in the art and that is capable of driving gene expression in the host cell of interest.

The present invention encompasses AHASL1 polynucleotide molecules and fragments and variants thereof. Polynucleotide molecules that are fragments of these nucleotide sequences are also encompassed by the present invention. By "fragment" is intended a portion of the nucleotide sequence encoding an AHASL1 protein of the invention. A fragment of an AHASL1 nucleotide sequence of the invention may encode a biologically active portion of an AHASL1 protein, or it may be a fragment that can be used as a hybridization probe or PCR primer using methods disclosed below. A biologically active portion of an AHASL1 protein can be prepared by isolating a portion of one of the AHASL1 nucleotide sequences of the invention, expressing the encoded portion of the AHASL1 protein (e.g., by recombinant expression in vitro), and assessing the activity of the encoded portion of the AHASL1 protein. Polynucleotide molecules that are fragments of an AHASL1 nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1500, 1600, 1700, 1800, 1900, or 1950 nucleotides, or up to the number of nucleotides present in a full-length nucleotide sequence disclosed herein (for example, 1968, 1968, 1716, and 1716 nucleotides for SEQ ID NOS: 1, 3, 5, and 7, respectively) depending upon the intended use.

A fragment of an AHASL1 nucleotide sequence that encodes a biologically active portion of an AHASL1 protein of the invention will encode at least about 15, 25, 30, 50, 75, 100, 125, 150, 175, 200, 250, 300, 350, 400, 450, 500, 550, 600, or 650 contiguous amino acids, or up to the total number of amino acids present in a full-length AHASL1 protein of the invention (for example, 655, 655, 571, and 571 amino acids for SEQ ID NOS: 2, 4, 6, and 8, respectively). Fragments of an AHASL1 nucleotide sequence that are useful as hybridization probes for PCR primers generally need not encode a biologically active portion of an AHASL1 protein.

Polynucleotide molecules that are variants of the nucleotide sequences disclosed herein are also encompassed by the present invention. "Variants" of the AHASL1 nucleotide sequences of the invention include those sequences that encode the AHASL1 proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the AHASL1 protein disclosed in the present invention as discussed below. Generally, nucleotide sequence variants of the invention will have at least about 75%, 80%, 85%, 90%, 91%, 92%, 93%, 94%, 95%, 96%, 97%, 98%, or 99% identity to a particular nucleotide sequence disclosed herein. A variant AHASL1 nucleotide sequence will encode an AHASL1 protein, respectively, that has an amino acid sequence having at least about 75%, 80%, 85%, 90%, 91%, 92%, 93%, 94%, 95%, 96%, 97%, 98%, or 99% identity to the amino acid sequence of an AHASL1 protein disclosed herein.

In addition, the skilled artisan will further appreciate that changes can be introduced by mutation into the nucleotide sequences of the invention thereby leading to changes in the amino acid sequence of the encoded AHASL1 proteins without altering the biological activity of the AHASL1 proteins. Thus, an isolated polynucleotide molecule encoding an AHASL1 protein having a sequence that differs from that of SEQ ID NOS: 1, 3, 5, or 7, respectively, can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of an AHASL1 protein (e.g., the sequence of SEQ ID NOS: 2, 4, 6, and 8, respectively) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif.

The proteins of the invention may be altered in various ways including amino acid substitutions, deletions, truncations, and insertions. Methods for such manipulations are generally known in the art. For example, amino acid sequence variants of the AHASL1 proteins can be prepared by mutations in the DNA. Methods for mutagenesis and nucleotide sequence alterations are well known in the art. See, for example, Kunkel (1985) *Proc. Natl. Acad. Sci. USA* 82:488492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Alternatively, variant AHASL1 nucleotide sequences can be made by introducing mutations randomly along all or part of an AHASL1 coding sequence, such as by saturation mutagenesis, and the resultant mutants can be screened for AHAS activity to identify mutants that retain AHAS activity, including herbicide-resistant AHAS activity. Following mutagenesis, the encoded protein can be expressed recombinantly, and the activity of the protein can be determined using standard assay techniques.

Thus, the nucleotide sequences of the invention include the sequences disclosed herein as well as fragments and variants thereof The AHASL1 nucleotide sequences of the invention, and fragments and variants thereof, can be used as probes and/or primers to identify and/or clone AHASL homologues in other plants. Such probes can be used to detect transcripts or genomic sequences encoding the same or identical proteins.

In this manner, methods such as PCR, hybridization, and the like can be used to identify such sequences having substantial identity to the sequences of the invention See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). AHASL nucleotide sequences isolated based on their sequence identity to the AHASL1 nucleotide sequences set forth herein or to fragments and variants thereof are encompassed by the present invention.

In a hybridization method, all or part of a known AHASL1 nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known AHASL1 nucleotide sequence disclosed herein. Degenerate primers designed on the basis of conserved nucleotides or amino acid residues in a known AHASL1 nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, 400, 500, 600, 700, 800, 900, 1000, 1200, 1400, 1600, or 1800 consecutive nucleotides of an AHASL1 nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, the entire AHASL1 sequence disclosed herein, or one or more portions thereof, may be used as a probe capable of specifically hybridizing to corresponding AHASL1 sequences and messenger RNAs. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the polynucleotide molecules and proteins of the invention encompass polynucleotide molecules and proteins comprising a nucleotide or an amino acid sequence that is sufficiently identical to the nucleotide sequence of SEQ ID NOS: 1, 3, 5, and/or 7, or to the amino acid sequence of SEQ ID NOS: 2, 4, 5, and/or 8. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 45%, 55%, or 65% identity, preferably 75% identity, more preferably 85%, 95%, or 98% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) Nucleic Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by AlignX in the software package Vector NTI Suite Version 7.

The AHASL1 nucleotide sequences of the invention include both the naturally occurring sequences as well as mutant forms, particularly mutant forms that encode AHASL1 proteins comprising herbicide-resistant AHAS activity. Likewise, the proteins of the invention encompass both naturally occurring proteins as well as variations and modified forms thereof. Such variants will continue to possess the desired AHAS activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by AHAS activity assays. See, for example, Singh et al. (1988) *Anal. Biochem.* 171:173-179, herein incorporated by reference.

Variant nucleotide sequences and proteins also encompass sequences and proteins derived from a mutagenic and recombinogenic procedure such as DNA shuffling. With such a procedure, one or more different AHASL coding sequences can be manipulated to create a new AHASL protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the AHASL1 gene of the invention and other known AHASL genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other dicots. In this manner, methods such as PCR, hybridization, and the like can be used to identify such sequences based on their sequence homology to the sequences set forth herein. Sequences isolated based on their sequence identity to the entire AHASL1 sequences set forth herein or to fragments thereof are encompassed by the present invention. Thus, isolated sequences that encode for an AHASL protein and which hybridize under stringent conditions to the sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

The AHASL1 polynucleotide sequences of the invention are provided in expression cassettes for expression in the plant of interest. The cassette will include 5' and 3' regulatory sequences operably linked to an AHASL1 polynucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the AHASL1 polynucleotide sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), an AHASL1 polynucleotide sequence of the invention, and a transcriptional and translational termination region (i.e., termination region) functional in plants. The promoter may be native or analogous, or foreign or heterologous, to the plant host and/or to the AHASL1 polynucleotide sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the AHASL1 polynucleotide sequence of the invention, it is intended that the promoter is not the native or naturally occurring promoter for the operably linked AHASL1 polynucleotide sequence of the invention. As used herein, a chimeric gene comprises a coding sequence operably linked to a transcription initiation region that is heterologous to the coding sequence.

While it may be preferable to express the AHASL1 polynucleotides of the invention using heterologous promoters, the native promoter sequences may be used. Such constructs would change expression levels of the AHASL1 protein in the plant or plant cell. Thus, the phenotype of the plant or plant cell is altered.

The termination region may be native with the transcriptional initiation region, may be native with the operably linked AHASL1 sequence of interest, may be native with the plant host, or may be derived from another source (i.e., foreign or heterologous to the promoter, the AHASL1 polynucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Nucleotide sequences for enhancing gene expression can also be used in the plant expression vectors. These include the introns of the maize AdhI, intronI gene (Callis et al. *Genes and Development* 1:1183-1200, 1987), and leader sequences, (W-sequence) from the Tobacco Mosaic virus (TMV), Maize Chlorotic Mottle Virus and Alfalfa Mosaic Virus (Gallie et al. *Nucleic Acid Res.* 15:8693-8711, 1987 and Skuzeski et al. *Plant Mol. Biol.* 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (*Plant Physiol.* 106:929-939, 1994) also have shown that introns are useful for regulating gene expression on a tissue specific basis. To further enhance or to optimize AHAS small subunit gene expression, the plant expression vectors of the invention may also contain DNA sequences containing matrix attachment regions (MARs). Plant cells transformed with such modified expression systems, then, may exhibit overexpression or constitutive expression of a nucleotide sequence of the invention.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced AHASL1 expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

In one embodiment, the nucleic acids of interest are targeted to the chloroplast for expression. In this manner, where the nucleic acid of interest is not directly inserted into the chloroplast, the expression cassette will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the AHASL polynucleotide of the invention such that the two sequences are contiguous and in the same reading frame. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481. While the AHASL1 proteins of the invention include a native chloroplast transit peptide, any chloroplast transit peptide known in art can be fused to the amino acid sequence of a mature AHASL1 protein of the invention by operably linking a choloroplast-targeting sequence to the 5'-end of a nucleotide sequence encoding a mature AHASL1 protein of the invention.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

As disclosed herein, the AHASL1 nucleotide sequences of the invention find use in enhancing the herbicide tolerance of plants that comprise in their genomes a gene encoding a herbicide-tolerant AHASL1 protein. Such a gene may be an endogenous gene or a transgene. Additionally, in certain embodiments, the nucleic acid sequences of the present invention can be stacked with any combination of polynucleotide sequences of interest in order to create plants with a desired phenotype. For example, the polynucleotides of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al. (1986) *Gene* 48:109). The combinations generated can also include multiple copies of any one of the polynucleotides of interest.

It is recognized that with these nucleotide sequences, antisense constructions, complementary to at least a portion of the messenger RNA (mRNA) for the AHASL1 polynucleotide sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

While the herbicide-resistant AHASL1 polynucleotides of the invention find use as selectable marker genes for plant transformation, the expression cassettes of the invention can include another selectable marker gene for the selection of transformed cells. Selectable marker genes, including those of the present invention, are utilized for the selection of transformed cells or tissues. Marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

The isolated polynucleotide molecules comprising nucleotide sequence that encode the AHASL1 proteins of the invention can be used in vectors to transform plants so that the plants created have enhanced resistant to herbicides, particularly imidazolinone herbicides. The isolated AHASL1 polynucleotide molecules of the invention can be used in vectors alone or in combination with a nucleotide sequence encoding the small subunit of the AHAS (AHASS) enzyme in conferring herbicide resistance in plants. See, U.S. Pat. No. 6,348,643; which is herein incorporated by reference.

The invention also relates to a plant expression vector comprising a promoter that drives expression in a plant operably linked to an isolated polynucleotide molecule of the invention. The isolated polynucleotide molecule comprises a nucleotide sequence encoding an AHASL1 protein, particularly an AHASL1 protein comprising an amino sequence that is set forth in SEQ ID NO: 2, 4, 6, or 8, or a functional fragment and variant thereof. The plant expression vector of the invention does not depend on a particular promoter, only that such a promoter is capable of driving gene expression in a plant cell. Preferred promoters include constitutive promoters and tissue-preferred promoters.

The transformation vectors of the invention can be used to produce plants transformed with a gene of interest. The transformation vector will comprise a selectable marker gene of the invention and a gene of interest to be introduced and typically expressed in the transformed plant. Such a selectable marker gene comprises a herbicide-resistant AHASL1 polynucleotide of the invention operably linked to a promoter that drives expression in a host cell. For use in plants and plant cells, the transformation vector comprises a selectable marker gene comprising a herbicide-resistant AHASL1 polynucleotide of the invention operably linked to a promoter that drives expression in a plant, cell.

The genes of interest of the invention vary depending on the desired outcome. For example, various changes in phenotype can be of interest including modifying the fatty acid composition in a plant, altering the amino acid content of a plant, altering a plant's insect and/or pathogen defense mechanisms, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

In one embodiment of the invention, the genes of interest include insect resistance genes such as, for example, *Bacillus thuringieinsis* toxin protein genes (U.S. Pat. Nos. 5,366,892; 5,747,450; 5,736,514; 5,723,756; 5,593,881; and Geiser et al. (1986) *Gene* 48:109).

The AHASL1 proteins or polypeptides of the invention can be purified from, for example, sunflower plants and can be used in compositions. Also, an isolated polynucleotide molecule encoding an AHASL1 protein of the invention can be used to express an AHASL1 protein of the invention in a microbe such as *E. coli* or a yeast. The expressed AHASL1 protein can be purified from extracts of *E. coli* or yeast by any method known to those or ordinary skill in the art.

The invention also relates to a method for creating a transgenic plant that is resistant to herbicides, comprising transforming a plant with a plant expression vector comprising a promoter that drives expression in a plant operably linked to an isolated polynucleotide molecule of the invention. The isolated polynucleotide molecule comprises a nucleotide sequence encoding an AHASL1 protein of the invention, particularly an AHASL1 protein comprising: an amino sequence that is set forth in SEQ ID NO: 2 or 6, an amino acid sequence encoded by SEQ ID NO: 1 or 5, or a functional fragment and variant of said amino acid sequences.

The invention also relates to the non-transgenic sunflower plants, transgenic plants produced by the methods of the invention, and progeny and other descendants of such non-transgenic and transgenic plants, which plants exhibit enhanced or increased resistance to herbicides that interfere with the AHAS enzyme, particularly imidazolinone and sulfonylurea herbicides.

The AHASL1 polynucleotides of the invention, particularly those encoding herbicide-resistant AHASL1 proteins, find use in methods for enhancing the resistance of herbicide-tolerant plants. In one embodiment of the invention, the herbicide-tolerant plants comprise a herbicide-tolerant or herbicide resistant AHASL protein. The herbicide-tolerant plants include both plants transformed with a herbicide-tolerant AHASL nucleotide sequences and plants that comprise in their genomes an endogenous gene that encodes a herbicide-tolerant AHASL protein. Nucleotide sequences encoding herbicide-tolerant AHASL proteins and herbicide-tolerant plants comprising an endogenous gene that encodes a herbicide-tolerant AHASL protein include the polynucleotides and plants of the present invention and those that are known in the art. See, for example, U.S. Pat. Nos. 5,013,659, 5,731,180, 5,767,361, 5,545,822, 5,736,629, 5,773,703, 5,773,704, 5,952,553 and 6,274,796; all of which are herein incorporated by reference. Such methods for enhancing the resistance of herbicide-tolerant plants comprise transforming a herbicide-tolerant plant with at least one polynucleotide construction comprising a promoter that drives expression in a plant cell that is operably linked to a herbicide resistant AHASL1 polynucleotide of the invention, particularly the polynucleotide encoding a herbicide-resistant AHASL1 protein set forth in SEQ ID NO: 1 or 5, polynucleotides encoding the amino acid sequence set forth in SEQ ID NO: 2 or 6, and fragments and variants said polynucleotides that encode polypeptides comprising herbicide-resistant AHAS activity.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo Chin Sci. Bull. 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:5.82-586; Hartman, et al. (1994) *Bio-Technology* 12:919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, an AHASL1 nucleotide sequence is operably linked to a plant promoter that is known for high-level expression in a plant cell, and this construct is then introduced into a plant that that is susceptible to an imidazolinone herbicide and a transformed plant it regenerated. The transformed plant is tolerant to exposure to a level of an imidazolinone herbicide that would kill or significantly injure an untransformed plant. This method can be applied to any plant species; however, it is most beneficial when applied to crop plants, particularly crop plants that are typically grown in the presence of at least one herbicide, particularly an imidazolinone herbicide.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.*, 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, Agrobacterium-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996)

*Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the an AHASL1 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago saliva*), rice (*Oryza saliva*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum, T. Turgidum* ssp. *duium*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

The herbicide resistant plants of the invention find use in methods for controlling weeds. Thus, the present invention further provides a method for controlling weeds in the vicinity of a herbicide-resistant plant of the invention. The method comprises applying an effective amount of a herbicide to the weeds and to the herbicide-resistant plant, wherein the plant has increased resistance to at least one herbicide, particularly an imidazolinone or sulfonylurea herbicide, when compared to a wild-type plant. In such a method for controlling weeds, the herbicide-resistant plants of the invention are preferably crop plants, including, but not limited to, sunflower, alfalfa, *Brassica* sp., soybean, cotton, safflower, peanut, tobacco, tomato, potato, wheat, rice, maize, sorghum, barley, rye, millet, and sorghum.

By providing plants having increased resistance to herbicides, particularly imidazolinone and sulfonylurea herbicides, a wide variety of formulations can be employed for protecting plants from weeds, so as to enhance plant growth and reduce competition for nutrients. A herbicide can be used by itself for pre-emergence, post-emergence, pre-planting and at planting control of weeds in areas surrounding the plants described herein or an imidazolinone herbicide formulation can be used that contains other additives. The herbicide can also be used as a seed treatment. That is an effective concentration organ effective amount of the herbicide, or a composition comprising an effective concentration or an effective amount of the herbicide can be applied directly to the seeds prior to or during the sowing of the seeds. Additives found in an imidazolinone or sulfonylurea herbicide formulation or composition include other herbicides, detergents, adjuvants, spreading agents, sticking agents, stabilizing agents, or the like. The herbicide formulation can be a wet or dry preparation and can include, but is not limited to, flowable powders, emulsifiable concentrates and liquid concentrates. The herbicide and herbicide formulations can be applied in accordance with conventional methods, for example, by spraying, irrigation, dusting, coating, and the like.

The present invention provides non-transgenic and transgenic seeds with increased resistance to at least one herbicide, particularly an AHAS-inhibiting herbicide. Such seeds include, for example, non-transgenic sunflower seeds comprising the herbicide-resistance characteristics of the plant with ATCC Patent Deposit Number PTA-6084, and transgenic seeds comprising a polynucleotide molecule of the invention that encodes a herbicide-resistant AHASL1 protein.

The present invention provides methods for producing a herbicide-resistant plant, particularly a herbicide-resistant sunflower plant, through conventional plant breeding involving sexual reproduction. The methods comprise crossing a first plant that is resistant to a herbicide to a second plant that is not resistant to the herbicide. The first plant can be any of the herbicide resistant plants of the present invention including, for example, transgenic plants comprising at least one of the polynucleotides of the present invention that encode a herbicide resistant AHASL and non-transgenic sunflower plants that comprise the herbicide-resistance characteristics of the sunflower plant with ATCC Patent Deposit Number PTA-6084. The second plant can be any plant that is capable of producing viable progeny plants (i.e., seeds) when crossed with the first plant. Typically, but not necessarily, the first and second plants are of the same species. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide resistance characteristics of the first plant.

The present invention further provides methods for increasing the herbicide-resistance of a plant, particularly a herbicide-resistant sunflower plant, through conventional plant breeding involving sexual reproduction. The methods comprise crossing a first plant that is resistant to a herbicide to a second plant that may or may not be resistant to the herbicide or may be resistant to different herbicide or herbicides than the first plant. The first plant can be any of the herbicide resistant plants of the present invention including, for example, transgenic plants comprising at least one of the polynucleotides of the present invention that encode a herbicide resistant AHASL and non-transgenic sunflower plants that comprise the herbicide-resistance characteristics of the sunflower plant with ATCC Patent Deposit Number PTA-6084. The second plant can be any plant that is capable of producing viable progeny plants (i.e., seeds) when crossed with the first plant. Typically, but not necessarily, the first and second plants are of the same species. The progeny plants produced by this method of the present invention have increased resistance to a herbicide when compared to either the first or second plant or both. When the first and second plants are resistant to different herbicides, the progeny plants will have the combined herbicide resistance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The methods of the invention can additionally involve selecting plants that comprise the herbicide resistance characteristics of the first plant, the second plant, or both the first and the second plant.

The present invention provides methods that involve the use of an AHAS-inhibiting herbicide. In these methods, the AHAS-inhibiting herbicide can be applied by any method known in the art including, but not limited to, seed treatment, soil treatment, and foliar treatment.

Prior to application, the AHAS-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NM, NOP), acetates (glycol diacetate), glycols, fatty acid dimethylamides, fatty acids and fatty acid esters. In principle, solvent mixtures may also be used.

Examples of suitable carriers are ground natural minerals (for example kaolins, clays, talc, chalk) and ground synthetic minerals (for example highly disperse silica, silicates).

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example Dichlorophen und enzylalkoholhemiformal.

Seed Treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans. polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

An examples of a suitable gelling agent is carrageen (Satiagel®)

Powders, materials for spreading, and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the AHAS-inhibiting herbicide. In this case, the AHAS-inhibiting herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight.

The AHAS-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the AHAS-inhibiting herbicide according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The AHAS-inhibiting herbicide may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

Ten parts by weight of the AHAS-inhibiting herbicide are dissolved in 90 parts by weight of water or a water-soluble solvent. As an alternative, wetters or other auxiliaries are added. The AHAS-inhibiting herbicide dissolves upon dilution with water, whereby a formulation with 10% (w/w) of AHAS-inhibiting herbicide is obtained.

B) Dispersible Concentrates (DC)

Twenty parts by weight of the AHAS-inhibiting herbicide are dissolved in 70 parts by weight of cyclohexanone with addition of 10 parts by weight of a dispersant, for example polyvinylpyrrolidone. Dilution with water gives a dispersion, whereby a formulation with 20% (w/w) of AHAS-inhibiting herbicide is obtained.

C) Emulsifiable Concentrates (EC)

Fifteen parts by weight of the AHAS-inhibiting herbicide are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of AHAS-inhibiting herbicide is obtained.

D) Emulsions (EW, EO, ES)

Twenty-five parts by weight of the AHAS-inhibiting herbicide are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of AHAS-inhibiting herbicide is obtained.

E) Suspensions (SC, OD, FS)

In an agitated ball mill, 20 parts by weight of the AHAS-inhibiting herbicide are comminuted with addition of 10 parts by weight of dispersants, wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained.

F) Water-Dispersible Granules and Water-Soluble Granules (WG, SG)

Fifty parts by weight of the AHAS-inhibiting herbicide are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the AHAS-inhibiting herbicide, whereby a formulation with 50% (w/w) of AHAS-inhibiting herbicide is obtained.

G) Water-Dispersible Powders and Water-Soluble Powders (WP, SP, SS, WS)

Seventy-five parts by weight of the AHAS-inhibiting herbicide are ground in a rotor-stator mill with addition of 25 parts by weight of dispersants, wetters and silica gel. Dilution with water gives a stable dispersion or solution of the AHAS-inhibiting herbicide, whereby a formulation with 75% (w/v) of AHAS-inhibiting herbicide is obtained.

I) Gel-Formulation (GF)

In an agitated ball mill, 20 parts by weight of the AHAS-inhibiting herbicide are comminuted with addition of 10 parts by weight of dispersants, 1 part by weight of a gelling agent wetters and 70 parts by weight of water or of an organic solvent to give a fine AHAS-inhibiting herbicide suspension. Dilution with water gives a stable suspension of the AHAS-inhibiting herbicide, whereby a formulation with 20% (w/w) of AHAS-inhibiting herbicide is obtained. This gel formulation is suitable for us as a seed treatment.

2. Products to be applied undiluted for foliar applications. For seed treatment purposes, such products may be applied to the seed diluted.

A) Dustable Powders (DP, DS)

Five parts by weight of the AHAS-inhibiting herbicide are ground finely and mixed intimately with 95 parts by weight of finely divided kaolin. This gives a dustable product having 5% (w/w) of AHAS-inhibiting herbicide.

B) Granules (GR, FG, GG, MG)

One-half part by weight of the AHAS-inhibiting herbicide is ground finely and associated with 95.5 parts by weight of carriers, whereby a formulation with 0.5% (w/w) of AHAS-inhibiting herbicide is obtained. Current methods are extrusion, spray-drying or the fluidized bed. This gives granules to be applied undiluted for foliar use.

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

The present invention non-transgenic and transgenic seeds of the herbicide-resistant plants of the present invention. Such seeds include, for example, non-transgenic sunflower seeds comprising the herbicide-resistance characteristics of the plant with ATCC Patent Deposit Number PTA-6084, and transgenic seeds comprising a polynucleotide molecule of the invention that encodes a herbicide-resistant AHASL1 protein.

For seed treatment, seeds of the herbicide resistant plants according of the present invention are treated with herbicides, preferably herbicides selected from the group consisting of AHAS-inhibiting herbicides such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid, pyrithiobac, and mixtures thereof, or with a formulation comprising a AHAS-inhibiting herbicide.

The term seed treatment comprises all suitable seed treatment techniques known in the art, such as seed dressing, seed coating, seed dusting, seed soaking, and seed pelleting.

In accordance with one variant of the present invention, a further subject of the invention is a method of treating soil by the application, in particular into the seed drill: either of a granular formulation containing the AHAS-inhibiting herbicide as a composition/formulation (e.g. a granular formulation, with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising at least one ALS inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed treatment application with the AHAS-inhibiting herbicide or with a formulation comprising the AHAS-inhibiting herbicide is carried out by spraying or dusting the seeds before sowing of the plants and before emergence of the plants.

In the treatment of seeds, the corresponding formulations are applied by treating the seeds with an effective amount of the AHAS-inhibiting herbicide or a formulation comprising the AHAS-inhibiting herbicide. Herein, the application rates are generally from 0.1 g to 10 kg of the a.i. (or of the mixture of a.i. or of the formulation) per 100 kg of seed, preferably from 1 g to 5 kg per 100 kg of seed, in particular from 1 g to 2.5 kg per 100 kg of seed. For specific crops such as lettuce the rate can be higher.

The present invention provides a method for combating undesired vegetation or controlling weeds comprising contacting the seeds of the resistant plants according to the present invention before sowing and/or after pregermination with an AHAS-inhibiting herbicide. The method can further comprise sowing the seeds, for example, in soil in a field or in a potting medium in greenhouse. The method finds particular use in combating undesired vegetation or controlling weeds in the immediate vicinity of the seed.

The control of undesired vegetation is understood as meaning the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon,*

*Emex, Datura, Viola, Galeopsis, Papaver, Centaurea, Trifolium, Ranunculus,* and *Taraxacum*. Monocotyledonous weeds include, but are not limited to, weeds of of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

In addition, the weeds of the present invention can include, for example, crop plants that are growing in an undesired location. For example, a volunteer maize plant that is in a field that predominantly comprises soybean plants can be considered as a weed, if the maize plant is undesired in the field of soybean plants.

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

Example 1

Mutagenesis of *Helianthus annuus* Line HA89 and Selection of Imidazolinone-Resistant Plants In the fall of growing season 1, sunflower plants (*Helianthus annuus*) of the maintainer line HA89 were treated with ethyl methanesulfonate (EMS, also referred to as methanesulfonic acid ethyl ester). EMS is a known mutagen that typically induces G·C-to-A·T transitions in DNA (Jander et al. (2003) *Plant Physiol.* 131:139-146). Two separate experiments were conducted. In the first experiment, three concentrations of EMS were used. Plants were treated with a solution comprising 0.1%, 1%, or 10% (w/v) EMS. For each EMS treatment, 14 rows of seeds were sown outdoors at the Advanta Semillas Biotech Research Station in Balcarce, BsAs, Argentina.

In the second experiment, 25 rows of line HA89 sunflower seeds were sown outdoors at the Advanta Winter Nursery in Oran, Salta, Argentina. Of these 25 rows, 8 rows were treated with 5% EMS as described above. The remaining 17 rows were untreated.

For each of the experiments, all $M_0$ plants were bagged prior to flowering in order to ensure that the resulting M1 seeds were the product of self-pollination. The seed heads from each EMS treatment were harvested and threshed in bulk. The following growing season, the mutated $M_1$ seeds from plants that were treated with 0.1%, 1.0%, 5.0% or 10.0% EMS were sown outdoors with each treatment in a separate plot. Twenty days later, when the plants were at the 2-4 leaf pair developmental stage, all of the EMS-treated plants were sprayed with 2× of Sweeper 70DG (100 g a.i./ha). The active ingredient in Sweeper is imazamox. After the herbicide spraying, a total of 53 plants survived and were selected as putative resistant. The distribution of resistant plants per EMS treatment is indicated in Table 1.

TABLE 1

Number of $M_1$ Imidazolinone-Resistant Sunflower Plants Recovered from Each EMS Treatment

| EMS Concentration (%) | No. of Resistant Plants Recovered |
| --- | --- |
| 0.1 | 14 |
| 1 | 18 |
| 5 | 5 |
| 10 | 16 |

Tissue samples were taken from each individual surviving $M_1$ plant and DNA from each sample was extracted for PCR amplification and sequencing studies described below in Example 2.

The 53 putative resistant plants (Table 1) were allowed to mature in the field. Of these 53 plants, 29 produced $M_2$ seeds, and these seeds were harvested. Shortly thereafter each of these $M_{1:2}$ families was sown in a separate plot (i.e., 29 plots, of 1 to 3 rows each in Fargo, N.D., USA. These $M_{1:2}$ families, and susceptible (wild-type) HA89 control plants, were sprayed with 0.5× of Sweeper (25 g a.i./ha). Eleven days after the herbicide treatment, three families were identified for which greater than 50% of the plants survived the herbicide treatment. Before flowering, the surviving plants in each these three $M_{1:2}$ families were bagged in order to produce self-pollinated $M_3$ seed. Individual heads from each $M_{1:2}$ plant were harvested and threshed. Individual $M_2$ plant tissue from selected families was harvested.

Example 2

PCR Amplification and Sequencing of Sunflower Polynucleotides Encoding Imidazolinone-Resistant and Wild-Type AHASL1 Proteins DNA was extracted from $M_1$ tissue of one of the three the $M_{1:2}$ families that were described above in Example 1. The DNA from this $M_1$ plant was subjected to amplification by polymerase chain reaction (PCR) and sequenced to determine the origin of the imidazolinone tolerance described in detail below.

The $M_1$ plant from this family was designated as MUT28. Genomic DNA was isolated from MUT28 tissue and also from tissue of a wild-type HA89 plant. The isolated DNA samples from MUT28 and HA89 were each diluted to a stock concentration of 100 ng/μL for use as template DNA for PCR amplifications. The entire coding region of the sunflower AHASL1 gene was amplified from the MUT28 and HA89 DNA samples. The specific primers used to obtain each amplicon are set forth in Table 2.

TABLE 2

PCR Primers for Amplifying the Coding Region of the Sunflower AHASL1 Gene

| Region of AHAS1 | Primer Name | Primer Sequence |
| --- | --- | --- |
| 1st amplicon (843 bp) | ALS1-1F | CATCATCATTAAATAACCAGAC (SEQ ID NO: 11) |
| | ALS1-1R | AACCCGGTAACCTCATCGGTTC (SEQ ID NO: 12) |

TABLE 2-continued

PCR Primers for Amplifying the Coding Region of the Sunflower AHASL1 Gene

| Region of AHAS1 | Primer Name | Primer Sequence |
|---|---|---|
| 2$^{nd}$ amplicon (739 bp) | ALS1-2F | CCCGGTTTTGATAGATGTACCG (SEQ ID NO: 13) |
| | ALS1-2R | CTGAGCAGCCCACATCTGATGT (SEQ ID NO: 14) |
| 3$^{rd}$ amplicon (674 bp) | ALS1-3F | CTGAGCAGCCCACATCTGATGT (SEQ ID NO: 15) |
| | ALS1-3R | AATTACACAACAAAACATTAAC (SEQ ID NO: 16) |

From comparisons of the nucleotide sequences of known AHASL1, AHASL2, and AHASL3 genes, PCR primers were designed to specifically amplify the AHASL1 gene from sunflower. The following PCR conditions were used in a total reaction volume of 25 µl: 1× buffer (Invitrogen Corp., Carlsbad, Calif., USA), 0.2 mM dNTPs (Invitrogen), 2.5 mM MgCl$_2$ (Invitrogen), 0.2 µM of each primer, 0.5 µL of Platinum Taq (5 U/µL) (Invitrogen) and 100 ng of genomic DNA. PCR reactions were carried out in a GeneAmp PCR System 9700 (PerkinElmer, Inc., Boston, Mass., USA). Cycling conditions were: an initial denaturation step at 94° C. for 1 minute followed by 35 cycles consisting of 94° C. for 45 seconds, 52° C. for 45 seconds and 72° C. for 70 seconds, and a final elongation step of 72° C. for 10 minutes. Two microliters of each resulting PCR product were then analyzed by agarose gel electrophoresis and concentration of DNA estimated by comparison to Low DNA Mass Ladder (Invitrogen Corp., Carlsbad, Calif., USA). The remaining PCR product was purified using Wizard® SV Gel and PCR Clean-Up System (Promega Corp., Madison, Wis., USA). The purified PCR products were then cycle-sequenced using a BigDye® Terminator v3.1 Cycle Sequencing Kit (Applied Biosystems, Foster City, Calif., USA) following the manufacturer's instructions. In addition to the primers used for the PCR amplifications (Table 2), additional primers set forth in Table 3 were used to complete the sequencing of the entire coding region of the sunflower AHASL1 gene.

TABLE 3

Additional Primers for Sequencing the Coding Region of the Sunflower AHASL1 gene

| Region of AHAS1 | Primer Name | Primer Sequence |
|---|---|---|
| 1$^{st}$ amplicon | ALS-3F | GCGCTGTTAGACAGTGTCC (SEQ ID NO: 17) |
| 2$^{nd}$ amplicon | SUNALS1F1 | ACTAATCTTGATTTTTCG (SEQ ID NO: 18) |
| 3$^{rd}$ amplicon | ALS-6R | CGGCAGATTTTCAACACGGA (SEQ ID NO: 19) |

Fluorescent-labeled products from sequencing reactions were resolved by capillary electrophoresis on an ABI Prism 310 Genetic Analyzer (Applied Biosystems) and analyzed using the ABI Prism DNA Sequencing Analysis Software, version 3.7. The sunflower AHASL1 sequencing files obtained from each amplicon were assembled using the Vector NTI Suite-Contig Express software, version 7.0 (InforMax, Frederick, Md., USA). The resulting DNA sequences were aligned with AHASL1 polynucleotide sequences of the HA89 sunflower line and *Xanthium* sp. (FIG. 1). The predicted amino acid sequence from the new mutant sunflower AHASL1 gene was aligned with the AHASL1 amino acid sequences of HA89 and *Xanthium* sp. (FIG. 2) using Vector NTI Suite-AlignX software, version 7.0 (InforMax) was used with default parameters. Single nucleotide polymorphisms and amino acid changes were then identified.

Example 3

The Herbicide-Resistance of MUT28 Sunflower Plants

To evaluate the resistance of MUT28 sunflower plants to an imidazolinone herbicides, HA89 (wild-type), MUT28 (homozygous), and HA89/MUT28 (heterozygous) sunflower plants were planted outdoors in Balcarce, Argentina during the growing season in a randomized complete block design (RCBD) field trial with two replications to evaluate the tolerance of the MUT28 and HA89/MUT28 plants to three rates of Sweeper 70DG: 1×, 2×, and 3×. The active ingredient in Sweeper is imazamox and the 1× dose is 50 g a.i./ha. The results are presented in Table 4.

TABLE 4

Imidazolinone Tolerance of MUT28 Sunflower Plants (Herbicide Injury Ratings)

| | RATE | | |
|---|---|---|---|
| LINE | 0× | 1× | 2× |
| HA89 | 0* | 75 | 75 |
| MUT28 across families | 0 | 33 | — |
| HA89/MUT28 | 0 | 28 | 45 |
| IMISUN-1 | 0 | 4 | 9 |

*No injury = 0

Compared to wild-type HA89, the MUT28 sunflower lines had less injury at the 1× rate of Sweeper. The HA89/MUT28 line also had less injury in this trial than HA89 at both the 1× and 2× rates of Sweeper. The results of this trial demonstrate that both the MUT28 (homozygous) and HA89/MUT28 (heterozygous) lines have increased tolerance to an imidazolinone herbicide, particularly imazamox. However, neither MUT28 nor HA89/MUT28 displayed the level of tolerance of the IMISUN-1 sunflower lines which is known to be homozygous for an AHASL1 gene encoding an AHASL1 protein having an Ala$_{190}$-to-Val substitution.

In a separate trial in Balcarce that was similar to the one described immediately above, the MUT28 line did not display any increased tolerance to Sweeper relative to HA89. However, in another separate trial conducted in Fargo, N.D., USA, 52% of M2 MUT28 plants were tolerant but displayed a lower level of tolerance than the SURES-1 line. SURES-1 is an sulfonylura-resistant, F3-derived F4 oilseed maintainer that was developed from plants of a wild *Helianthus annuus* population collected in Kansas, USA (Al-Khatib et al. (1999) "Survey of common sunflower (*Helianthus annuus*) resistance to ALS-inhibiting herbicides in northeast Kansas," In: *Proceedings of 21th Sunflower Research Workshop*, National Sunflower Association, Bismarck, N.D., pp 210-215).

To evaluate the tolerance of MUT28 sunflower plants to sulfonylurea herbicides, HA89 (wild-type), MUT28, IMISUN-1, and SURES-1 sunflower lines were planted outdoors in Balcarce, Argentina during the growing season in an RCBD field trial with two replications to evaluate the tolerance of MUT28 plants to the sulfonylurea herbicide thifensulfuron (TFS) at 1× and 2× rates. The 1× rates for TFS is 4.4 g a.i./ha. The results are presented in Table 5.

TABLE 5

Sulfonylurea Tolerance of MUT28 Sunflower Plants (Herbicide Injury Ratings)

| LINE | RATE | | |
|---|---|---|---|
| | 0× | 1× | 2× |
| HA89 | 0* | 75 | 75 |
| MUT28 | 0 | 30 | 42 |
| IMISUN-1 | 0 | 20 | 75 |
| SURES-1 | 0 | 5 | 3 |

*No injury = 0

The MUT28 line displayed better tolerance to TFS at both the 1× and 2× rates than HA89 demonstrating that the MUT28 plants have increased tolerance to a sulfonylurea herbicide when compared to a wild-type sunflower plants.

Example 4

Herbicide-Resistant Sunflower AHASL1 Proteins

The present invention discloses both the nucleotide and amino acid sequences for wild-type and herbicide resistant sunflower AHASL1 polypeptides. Plants comprising herbicide-resistant AHASL1 polypeptides have been previously identified, and a number of conserved regions of AHASL1 polypeptides that are the sites of amino acids substitutions that confer herbicide resistance have been described. See, Devine and Eberlein (1997) "Physiological, biochemical and molecular aspects of herbicide resistance based on altered target sites". In: *Herbicide Activity: Toxicology, Biochemistry and Molecular Biology*, Roe et al. (eds.), pp. 159-185, IOS Press, Amsterdam; and Devine and Shukla, (2000) *Crop Protection* 19:881-889.

Using the AHASL1 sequences of the invention and methods known to those of ordinary skill in art, one can produce additional polynucleotides encoding herbicide resistant AHASL1 polypeptides having one, two, three, or more amino acid substitutions at the identified sites in these conserved regions. Table 6 provides the conserved regions of AHASL1 proteins, the amino acid substitutions known to confer herbicide resistance within these conserved regions, and the corresponding amino acids in the sunflower AHASL1 protein set forth in SEQ ID NO: 4.

TABLE 6

Mutations in conserved regions of AHASL1 polypeptides known to confer herbicide-resistance and their equivalent position in sunflower AHASL1

| Conserved region[1] | Mutation[2] | Reference | Amino acid position in sunflower |
|---|---|---|---|
| VFAYPGGASMEIHQALTRS[3] | $Ala_{122}$ to Thr | Bernasconi et al.[4] Wright & Penner[14] | $Ala_{107}$ |
| AITGQVPRRMIGT[3] | $Pro_{197}$ to Ala | Boutsalis et al.[6] | $Pro_{182}$[13] |
| | $Pro_{197}$ to Thr | Guttieri et al.[7] | |
| | $Pro_{197}$ to His | Guttieri et al.[8] | |
| | $Pro_{197}$ to Leu | Guttieri et al.[7] Kolkman et al.[15] | |
| | $Pro_{197}$ to Arg | Guttieri et al.[7] | |
| | $Pro_{197}$ to Ile | Boutsalis et al.[6] | |
| | $Pro_{197}$ to Gln | Guttieri et al.[7] | |
| | $Pro_{197}$ to Ser | Guttieri et al.[7] | |
| AFQETP[3] | $Ala_{205}$ to Asp | Hartnett et al.[9] | $Ala_{190}$ |
| | $Ala_{205}$ to Val | Simpson[10] Kolkman et al.[15] White et al.[16] | |
| QWED[3] | $Trp_{574}$ to Leu | Bruniard[11] Boutsalis et al.[6] | $Trp_{559}$ |

TABLE 6-continued

Mutations in conserved regions of AHASL1 polypeptides known to confer herbicide-resistance and their equivalent position in sunflower AHASL1

| Conserved region[1] | Mutation[2] | Reference | Amino acid position in sunflower |
|---|---|---|---|
| IPSGG[4] | Ser$_{653}$ to Asn | Devine & Eberlein[12] Lee et al.[17] | Ala$_{638}$ |
| | Ser$_{653}$ to Thr | Chang & Duggleby[18] | |
| | Ser$_{653}$ to Phe | | |

[1]Conserved regions from Devine and Eberlein (1997) "Physiological, biochemical and molecular aspects of herbicide resistance based on altered target sites". In: Herbicide Activity: Toxicology, Biochemistry and Molecular Biology, Roe et al. (eds.), pp. 159-185, IOS Press, Amsterdam and Devine and Shukla, (2000) Crop Protection 19: 881-889.
[2]Amino acid numbering corresponds to the amino acid sequence of the *Arabidopsis thaliana* AHASL1 polypeptide.
[3]Sunflower AHASL1 (SEQ ID NO: 4) has the same conserved region.
[4]The region of the sunflower AHASL1 (SEQ ID NO: 4) corresponding to this conserved region has the sequence IPAGG.
[5]Bernasconi et al. (1995) J. Biol. Chem. 270(29): 17381-17385.
[6]Boutsalis et al. (1999) Pestic. Sci. 55: 507-516.
[7]Guttieri et al. (1995) Weed Sci. 43: 143-178.
[8]Guttieri et al. (1992) Weed Sci. 40: 670-678.
[9]Hartnett et al. (1990) "Herbicide-resistant plants carrying mutated acetolactate synthase genes," In: Managing Resistance to Agrochemicals: Fundamental Research to Practical Strategies, Green et al. (eds.), American Chemical Soc. Symp., Series No. 421, Washington, DC, USA
[10]Simpson (1998) Down to Earth 53(1): 26-35.
[11]Bruniard (2001) Inheritance of imidazolinone resistance, characterization of cross-resistance pattern, and identification of molecular markers in sunflower (*Helianthus annuus* L.). Ph. D. Thesis, North Dakota State University, Fargo, ND, USA, pp 1-78.
[12]Devine and Eberlein (1997) "Physiological, biochemical and molecular aspects of herbicide resistance based on altered target sites". In: Herbicide Activity: Toxicology, Biochemistry and Molecular Biology, Roe et al. (eds.), pp. 159-185, IOS Press, Amsterdam
[13]The present invention discloses the amino acid sequence of a herbicide-resistant AHASL1 with the Pro$_{182}$ to Leu substitution (SEQ ID NO: 2) and a polynucleotide sequence encoding this herbicide resistant AHASL1 (SEQ ID NO: 1).
[14]Wright and Penner (1998) Theor. Appl. Genet. 96: 612-620.
[15]Kolkman et al. (2004) Theor. Appl. Genet. 109: 1147-1159.
[16]White et al. (2003) Weed Sci. 51: 845-853.
[17]Lee et al. (1999) FEBS Lett. 452: 341-345.
[18]Chang and Duggleby (1998) Biochem J. 333: 765-777.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A sunflower plant, wherein a representative sample of seed capable of producing the plant was deposited under ATCC Patent Deposit Number PTA-6084.

2. The sunflower plant of claim 1, wherein said plant has enhanced resistance to at least one herbicide selected from the group consisting of imidazolinone herbicides, sulfonylurea herbicides, triazolopyrimidine herbicides, pyrimidinyloxybenzoate herbicides, and sulfonylamino-carbonyltriazolinone herbicides.

3. A sunflower plant produced by transforming the plant of claim 1.

4. A seed of or capable of producing the sunflower plant of claim 1.

5. A method of controlling weeds in the vicinity of the sunflower plant of claim 1, said method comprising applying an effective amount of an imidazolinone herbicide, a sulfonylurea herbicide, a triazolopyrimidine herbicide, a pyrimidinyloxybenzoate herbicide, a sulfonylamino-carbonyltriazolinone herbicide, or mixture thereof to the weeds and to the sunflower plant.

6. The method of claim 5, wherein said imidazolinone herbicide is selected from the group consisting of: 2-(4-isopropyl-4-methly-5-oxo-2-imidiazolin-2-yl)-nicotinic acid 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl 6-(4-isopropyl-4- methyl-5-oxo-2-imidazolin-2-yl)-m-toluate and methyl 2-(4-isopropyl-4-methyl-5-oxo-2-imidazolin-2-yl)-p-toluate, and combinations thereof.

7. The method of claim 5, wherein said sulfonylurea herbicide is selected from the group consisting of chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluzasulfuron, imazosulfuron, pyrazosulfuron ethyl, halosulfuron, and mixtures thereof.

8. A method for producing a herbicide-resistant plant comprising crossing a first plant that is resistant to a herbicide to a second plant that is not resistant to the herbicide, wherein the first plant is the plant of claim 1.

9. The method of claim 8 further comprising selecting for a descendent plant that is resistant to the herbicide.

10. A herbicide-resistant plant produced by the method of claim 8.

11. A seed of the plant of claim 10, wherein said seed is capable of producing plants comprising the herbicide resistant characteristics of the first plant.

12. A method for increasing the herbicide-resistance of a plant comprising crossing a first plant to a second plant, wherein the first plant is the plant of claim 1.

13. The method of claim 12 further comprising selecting for a descendent plant that comprises increased herbicide resistance when compared to the herbicide resistance of said second plant.

14. A plant produced by the method of claim 12.

15. A seed of the plant of claim 14, wherein said seed is capable of producing plants comprising the increased herbicide resistance.

16. A seed of the plant of claim 1, wherein said seed is treated with an AHAS-inhibiting herbicide.

17. A method for combating undesired vegetation comprising contacting a seed of the plant of claim 1 before sowing and/or after pregermination with an AHAS-inhibiting herbicide.

18. The method of claim 16, wherein the AHAS-inhibiting herbicide is a sulfonylurea herbicide.

19. The method of claim 17, wherein the AHAS-inhibiting herbicide is a sulfonylurea herbicide.

20. A descendent of the plant of claim 1, wherein the descendent has the same herbicide resistance characteristic of the plant, wherein the descendent is obtained by conventional plant breeding.

21. A method of controlling weeds in the vicinity of the descendent of claim 20, the method comprising applying an effective amount of an imidazolinone herbicide, a sulfonylurea herbicide, a triazolopyrimidine herbicide, a pyrimidinyloxybenzoate herbicide, a sulfonylamino-carbonyltriazolinone herbicide, or mixtures thereof to the weeds and to the descendent.

* * * * *

SEQUENCE LISTING

<160> NUMBER OF SEQ ID NOS: 19

<210> SEQ ID NO 1
<211> LENGTH: 1968
<212> TYPE: DNA
<213> ORGANISM: Helianthus annus
<220> FEATURE:
<221> NAME/KEY: CDS
<222> LOCATION: (1)...(1968)
<220> FEATURE:
<221> NAME/KEY: misc_feature
<222> LOCATION: (0)...(0)
<223> OTHER INFORMATION: 1248-3

<400> SEQUENCE: 1

```
atg gcg gct cct ccc aac cct tcc atc tcc ttc aaa cca ccg tca ccc    48
Met Ala Ala Pro Pro Asn Pro Ser Ile Ser Phe Lys Pro Pro Ser Pro
```

-continued

```
  1               5                   10                  15
gcc gcc gca ctg cca cca cgc tcc gcc ttc ctc ccc cgt ttc gca tta      96
Ala Ala Ala Leu Pro Pro Arg Ser Ala Phe Leu Pro Arg Phe Ala Leu
                 20                  25                  30 ccc atc act tcc act acc caa aaa cga cac cgt ctt cac atc tcc aat     144
Pro Ile Thr Ser Thr Thr Gln Lys Arg His Arg Leu His Ile Ser Asn
             35                  40                  45 gtt ctc tcc gac tcc aaa tcc acc acc acc acc acc acc act caa         192
Val Leu Ser Asp Ser Lys Ser Thr Thr Thr Thr Thr Thr Thr Gln
 50                  55                  60 cga ccg tta ccg gtg cag cct ttt gtc tcc cgt tac gcg cca gat caa     240
Arg Pro Leu Pro Val Gln Pro Phe Val Ser Arg Tyr Ala Pro Asp Gln
 65                  70                  75                  80 ccg aga aaa ggc gca gac gtg ttg gtg gaa gct ctg gaa cgg gaa ggt     288
Pro Arg Lys Gly Ala Asp Val Leu Val Glu Ala Leu Glu Arg Glu Gly
                 85                  90                  95 gtc acc gac gtc ttc gcc tac ccc ggc ggc gcg tca atg gag atc cac     336
Val Thr Asp Val Phe Ala Tyr Pro Gly Gly Ala Ser Met Glu Ile His
             100                 105                 110 caa gct ctc acg cgc tca agc act atc cgc aat gtg ctc ccc cgt cac     384
Gln Ala Leu Thr Arg Ser Ser Thr Ile Arg Asn Val Leu Pro Arg His
         115                 120                 125 gaa cag ggc ggc gtg ttc gcc gcc gaa ggc tac gcg cgc gcc tcc ggt     432
Glu Gln Gly Gly Val Phe Ala Ala Glu Gly Tyr Ala Arg Ala Ser Gly
     130                 135                 140 ctt ccc ggc gtg tgt atc gcc act tcc ggt ccc gga gct acg aac cta     480
Leu Pro Gly Val Cys Ile Ala Thr Ser Gly Pro Gly Ala Thr Asn Leu
145                 150                 155                 160 gtt agt ggt ctt gct gac gcg ctg tta gac agt gtc ccc atg gtg gca     528
Val Ser Gly Leu Ala Asp Ala Leu Leu Asp Ser Val Pro Met Val Ala
                 165                 170                 175 atc acc ggt caa gtt ctc cgg aga atg atc gga acc gat gcg ttt caa     576
Ile Thr Gly Gln Val Leu Arg Arg Met Ile Gly Thr Asp Ala Phe Gln
             180                 185                 190 gaa acc cca att gtt gag gta aca cgt tcg atc act aaa cat aat tat     624
Glu Thr Pro Ile Val Glu Val Thr Arg Ser Ile Thr Lys His Asn Tyr
         195                 200                 205 ctt gtg ttg gat gtt gag gat att ccc aga att gtt cgt gag gct ttt     672
Leu Val Leu Asp Val Glu Asp Ile Pro Arg Ile Val Arg Glu Ala Phe
     210                 215                 220 tat ctt gcg agt tcg ggt cga ccc ggc ccg gtt ttg ata gat gta ccg     720
Tyr Leu Ala Ser Ser Gly Arg Pro Gly Pro Val Leu Ile Asp Val Pro
225                 230                 235                 240 aaa gat ata cag caa cag tta gtg gtg ccg aaa tgg gat gaa ccg atg     768
Lys Asp Ile Gln Gln Gln Leu Val Val Pro Lys Trp Asp Glu Pro Met
                 245                 250                 255 agg tta ccg ggt tat ttg tct aga atg ccg aag cct caa tat gat ggg     816
Arg Leu Pro Gly Tyr Leu Ser Arg Met Pro Lys Pro Gln Tyr Asp Gly
             260                 265                 270 cat ttg gaa cag att gtt agg ttg gtg ggg gaa gcg aag agg ccg gtt     864
His Leu Glu Gln Ile Val Arg Leu Val Gly Glu Ala Lys Arg Pro Val
         275                 280                 285 ttg tat gtg ggt ggt ggg tgt ttg aat tcg gat gat gag ttg agg cgg     912
Leu Tyr Val Gly Gly Gly Cys Leu Asn Ser Asp Asp Glu Leu Arg Arg
     290                 295                 300 ttt gtg gag ctt acg ggg att ccg gtt gcg agt act ttg atg ggg ctc     960
Phe Val Glu Leu Thr Gly Ile Pro Val Ala Ser Thr Leu Met Gly Leu
305                 310                 315                 320 gga gcg tac cct gct tcg agt gat ttg tcg ctt cat atg ctt ggg atg    1008
```

```
Gly Ala Tyr Pro Ala Ser Ser Asp Leu Ser Leu His Met Leu Gly Met
            325                 330                 335 cat ggt acg gtt tat gcg aat tat gcg gtt gat aag agt gat ttg ttg    1056
His Gly Thr Val Tyr Ala Asn Tyr Ala Val Asp Lys Ser Asp Leu Leu
        340                 345                 350 ctt gcg ttt ggg gtg cgg ttt gat gat cgt gtg acg ggg aag ctt gag    1104
Leu Ala Phe Gly Val Arg Phe Asp Asp Arg Val Thr Gly Lys Leu Glu
            355                 360                 365 gcg ttt gct agt agg gcg aag att gtt cat att gat att gat cct gct    1152
Ala Phe Ala Ser Arg Ala Lys Ile Val His Ile Asp Ile Asp Pro Ala
    370                 375                 380 gaa att ggg aag aat aag cag cct cat gtg tcg att tgt ggt gat att    1200
Glu Ile Gly Lys Asn Lys Gln Pro His Val Ser Ile Cys Gly Asp Ile
385                 390                 395                 400 aag gtc gcg tta cag ggt ttg aac aag att ttg gag gaa aag aat tcg    1248
Lys Val Ala Leu Gln Gly Leu Asn Lys Ile Leu Glu Glu Lys Asn Ser
                405                 410                 415 gtg act aat ctt gat ttt tcg acc tgg aga aag gaa ttg gat gaa caa    1296
Val Thr Asn Leu Asp Phe Ser Thr Trp Arg Lys Glu Leu Asp Glu Gln
            420                 425                 430 aaa atg aag ttc ccg ttg agc ttt aaa acg ttt ggc gaa gcg att cct    1344
Lys Met Lys Phe Pro Leu Ser Phe Lys Thr Phe Gly Glu Ala Ile Pro
        435                 440                 445 cca cag tat gct att caa gtt ctt gat gag tta acg ggc ggg aat gca    1392
Pro Gln Tyr Ala Ile Gln Val Leu Asp Glu Leu Thr Gly Gly Asn Ala
    450                 455                 460 att att agc acc ggt gtc ggg caa cat cag atg tgg gct gct cag ttt    1440
Ile Ile Ser Thr Gly Val Gly Gln His Gln Met Trp Ala Ala Gln Phe
465                 470                 475                 480 tac aaa tac aac aaa cct aga caa tgg ctg acg tcg ggc ggg cta ggg    1488
Tyr Lys Tyr Asn Lys Pro Arg Gln Trp Leu Thr Ser Gly Gly Leu Gly
                485                 490                 495 gca atg ggt ttc ggc ctg ccc gct gct atc ggg gcg gcc gtt gca aga    1536
Ala Met Gly Phe Gly Leu Pro Ala Ala Ile Gly Ala Ala Val Ala Arg
            500                 505                 510 cct gat gcg gta gta gtt gac atc gac ggt gac gga agc ttt atg atg    1584
Pro Asp Ala Val Val Val Asp Ile Asp Gly Asp Gly Ser Phe Met Met
        515                 520                 525 aat gtt caa gag tta gcc aca atc cgt gtt gaa aat ctg ccg gtt aag    1632
Asn Val Gln Glu Leu Ala Thr Ile Arg Val Glu Asn Leu Pro Val Lys
    530                 535                 540 att tta tta ctt aac aac cag cat ttg ggt atg gtg gtt cag tgg gag    1680
Ile Leu Leu Leu Asn Asn Gln His Leu Gly Met Val Val Gln Trp Glu
545                 550                 555                 560 gat cgg ttt tac aag gcg aat cgg gct cat acc tac tta gga aac ccg    1728
Asp Arg Phe Tyr Lys Ala Asn Arg Ala His Thr Tyr Leu Gly Asn Pro
                565                 570                 575 tca aaa gag tcg gaa ata ttc cct aac atg gtg aag ttt gct gaa gcc    1776
Ser Lys Glu Ser Glu Ile Phe Pro Asn Met Val Lys Phe Ala Glu Ala
            580                 585                 590 tgt gat atc ccg gct gct cga gtg acc caa aag gcg gat cta cga gca    1824
Cys Asp Ile Pro Ala Ala Arg Val Thr Gln Lys Ala Asp Leu Arg Ala
        595                 600                 605 gct att cag aag atg ttg gat aca ccc ggg cct tac ttg ttg gat gtg    1872
Ala Ile Gln Lys Met Leu Asp Thr Pro Gly Pro Tyr Leu Leu Asp Val
    610                 615                 620 att gtg ccg cat caa gaa cac gtg ttg ccc atg atc ccg gct ggc gga    1920
Ile Val Pro His Gln Glu His Val Leu Pro Met Ile Pro Ala Gly Gly
625                 630                 635                 640
```

```
ggt ttc tcg gat gtg atc acc gag ggt gat ggc aga acg aaa tat tga    1968
Gly Phe Ser Asp Val Ile Thr Glu Gly Asp Gly Arg Thr Lys Tyr *
                645                 650                 655
```

<210> SEQ ID NO 2
<211> LENGTH: 655
<212> TYPE: PRT
<213> ORGANISM: Helianthus annus

<400> SEQUENCE: 2

```
Met Ala Ala Pro Pro Asn Pro Ser Ile Ser Phe Lys Pro Pro Ser Pro
  1               5                  10                  15

Ala Ala Ala Leu Pro Pro Arg Ser Ala Phe Leu Pro Arg Phe Ala Leu
                 20                  25                  30

Pro Ile Thr Ser Thr Thr Gln Lys Arg His Arg Leu His Ile Ser Asn
             35                  40                  45

Val Leu Ser Asp Ser Lys Ser Thr Thr Thr Thr Thr Thr Thr Thr Gln
 50                  55                  60

Arg Pro Leu Pro Val Gln Pro Phe Val Ser Arg Tyr Ala Pro Asp Gln
 65                  70                  75                  80

Pro Arg Lys Gly Ala Asp Val Leu Val Glu Ala Leu Glu Arg Glu Gly
                 85                  90                  95

Val Thr Asp Val Phe Ala Tyr Pro Gly Gly Ala Ser Met Glu Ile His
                100                 105                 110

Gln Ala Leu Thr Arg Ser Ser Thr Ile Arg Asn Val Leu Pro Arg His
                115                 120                 125

Glu Gln Gly Gly Val Phe Ala Ala Glu Gly Tyr Ala Arg Ala Ser Gly
            130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Leu Arg Arg Met Ile Gly Thr Asp Ala Phe Gln
                180                 185                 190

Glu Thr Pro Ile Val Glu Val Thr Arg Ser Ile Thr Lys His Asn Tyr
            195                 200                 205

Leu Val Leu Asp Val Glu Asp Ile Pro Arg Ile Val Arg Glu Ala Phe
210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
                260                 265                 270

His Leu Glu Gln Ile Val Arg Leu Val Gly Glu Ala Lys Arg Pro Val
            275                 280                 285

Leu Tyr Val Gly Gly Gly Cys Leu Asn Ser Asp Asp Glu Leu Arg Arg
290                 295                 300

Phe Val Glu Leu Thr Gly Ile Pro Val Ala Ser Thr Leu Met Gly Leu
305                 310                 315                 320

Gly Ala Tyr Pro Ala Ser Ser Asp Leu Ser Leu His Met Leu Gly Met
                325                 330                 335

His Gly Thr Val Tyr Ala Asn Tyr Ala Val Asp Lys Ser Asp Leu Leu
            340                 345                 350

Leu Ala Phe Gly Val Arg Phe Asp Asp Arg Val Thr Gly Lys Leu Glu
```

```
                    355                 360                 365
Ala Phe Ala Ser Arg Ala Lys Ile Val His Ile Asp Ile Asp Pro Ala
        370                 375                 380

Glu Ile Gly Lys Asn Lys Gln Pro His Val Ser Ile Cys Gly Asp Ile
385                 390                 395                 400

Lys Val Ala Leu Gln Gly Leu Asn Lys Ile Leu Glu Glu Lys Asn Ser
                405                 410                 415

Val Thr Asn Leu Asp Phe Ser Thr Trp Arg Lys Glu Leu Asp Glu Gln
            420                 425                 430

Lys Met Lys Phe Pro Leu Ser Phe Lys Thr Phe Gly Glu Ala Ile Pro
        435                 440                 445

Pro Gln Tyr Ala Ile Gln Val Leu Asp Glu Leu Thr Gly Gly Asn Ala
    450                 455                 460

Ile Ile Ser Thr Gly Val Gly Gln His Gln Met Trp Ala Ala Gln Phe
465                 470                 475                 480

Tyr Lys Tyr Asn Lys Pro Arg Gln Trp Leu Thr Ser Gly Gly Leu Gly
                485                 490                 495

Ala Met Gly Phe Gly Leu Pro Ala Ala Ile Gly Ala Ala Val Ala Arg
            500                 505                 510

Pro Asp Ala Val Val Val Asp Ile Asp Gly Asp Gly Ser Phe Met Met
        515                 520                 525

Asn Val Gln Glu Leu Ala Thr Ile Arg Val Glu Asn Leu Pro Val Lys
    530                 535                 540

Ile Leu Leu Leu Asn Asn Gln His Leu Gly Met Val Val Gln Trp Glu
545                 550                 555                 560

Asp Arg Phe Tyr Lys Ala Asn Arg Ala His Thr Tyr Leu Gly Asn Pro
                565                 570                 575

Ser Lys Glu Ser Glu Ile Phe Pro Asn Met Val Lys Phe Ala Glu Ala
            580                 585                 590

Cys Asp Ile Pro Ala Ala Arg Val Thr Gln Lys Ala Asp Leu Arg Ala
        595                 600                 605

Ala Ile Gln Lys Met Leu Asp Thr Pro Gly Pro Tyr Leu Leu Asp Val
    610                 615                 620

Ile Val Pro His Gln Glu His Val Leu Pro Met Ile Pro Ala Gly Gly
625                 630                 635                 640

Gly Phe Ser Asp Val Ile Thr Glu Gly Asp Gly Arg Thr Lys Tyr
                645                 650                 655

<210> SEQ ID NO 3
<211> LENGTH: 1968
<212> TYPE: DNA
<213> ORGANISM: Helianthus annus
<220> FEATURE:
<221> NAME/KEY: CDS
<222> LOCATION: (1)...(1968)
<220> FEATURE:
<221> NAME/KEY: misc_feature
<222> LOCATION: (0)...(0)
<223> OTHER INFORMATION: HA89

<400> SEQUENCE: 3 atg gcg gct cct ccc aac cct tcc atc tcc ttc aaa cca ccg tca ccc        48
Met Ala Ala Pro Pro Asn Pro Ser Ile Ser Phe Lys Pro Pro Ser Pro
 1               5                  10                  15 gcc gcc gca ctg cca cca cgc tcc gcc ttc ctc ccc cgt ttc gca tta        96
Ala Ala Ala Leu Pro Pro Arg Ser Ala Phe Leu Pro Arg Phe Ala Leu
            20                  25                  30
```

```
ccc atc act tcc act acc caa aaa cga cac cgt ctt cac atc tcc aat      144
Pro Ile Thr Ser Thr Thr Gln Lys Arg His Arg Leu His Ile Ser Asn
         35                  40                  45 gtt ctc tcc gac tcc aaa tcc acc acc acc acc acc acc act caa          192
Val Leu Ser Asp Ser Lys Ser Thr Thr Thr Thr Thr Thr Thr Gln
 50                  55                  60 cga ccg tta ccg gtg cag cct ttt gtc tcc cgt tac gcg cca gat caa      240
Arg Pro Leu Pro Val Gln Pro Phe Val Ser Arg Tyr Ala Pro Asp Gln
 65                  70                  75                  80 ccg aga aaa ggc gca gac gtg ttg gtg gaa gct ctg gaa cgg gaa ggt      288
Pro Arg Lys Gly Ala Asp Val Leu Val Glu Ala Leu Glu Arg Glu Gly
                 85                  90                  95 gtc acc gac gtc ttc gcc tac ccc ggc ggc gcg tca atg gag atc cac      336
Val Thr Asp Val Phe Ala Tyr Pro Gly Gly Ala Ser Met Glu Ile His
                 100                 105                 110 caa gct ctc acg cgc tca agc act atc cgc aat gtg ctc ccc cgt cac      384
Gln Ala Leu Thr Arg Ser Ser Thr Ile Arg Asn Val Leu Pro Arg His
         115                 120                 125 gaa cag ggc ggc gtg ttc gcc gcc gaa ggc tac gcg cgc gcc tcc ggt      432
Glu Gln Gly Gly Val Phe Ala Ala Glu Gly Tyr Ala Arg Ala Ser Gly
         130                 135                 140 ctt ccc ggc gtg tgt atc gcc act tcc ggt ccc gga gct acg aac cta      480
Leu Pro Gly Val Cys Ile Ala Thr Ser Gly Pro Gly Ala Thr Asn Leu
145                 150                 155                 160 gtt agt ggt ctt gct gac gcg ctg tta gac agt gtc ccc atg gtg gca      528
Val Ser Gly Leu Ala Asp Ala Leu Leu Asp Ser Val Pro Met Val Ala
                 165                 170                 175 atc acc ggt caa gtt ccc cgg aga atg atc gga acc gat gcg ttt caa      576
Ile Thr Gly Gln Val Pro Arg Arg Met Ile Gly Thr Asp Ala Phe Gln
                 180                 185                 190 gaa acc cca att gtt gag gta aca cgt tcg atc act aaa cat aat tat      624
Glu Thr Pro Ile Val Glu Val Thr Arg Ser Ile Thr Lys His Asn Tyr
         195                 200                 205 ctt gtg ttg gat gtt gag gat att ccc aga att gtt cgt gag gct ttt      672
Leu Val Leu Asp Val Glu Asp Ile Pro Arg Ile Val Arg Glu Ala Phe
         210                 215                 220 tat ctt gcg agt tcg ggt cga ccc ggc ccg gtt ttg ata gat gta ccg      720
Tyr Leu Ala Ser Ser Gly Arg Pro Gly Pro Val Leu Ile Asp Val Pro
225                 230                 235                 240 aaa gat ata cag caa cag tta gtg gtg ccg aaa tgg gat gaa ccg atg      768
Lys Asp Ile Gln Gln Gln Leu Val Val Pro Lys Trp Asp Glu Pro Met
                 245                 250                 255 agg tta ccg ggt tat ttg tct aga atg ccg aag cct caa tat gat ggg      816
Arg Leu Pro Gly Tyr Leu Ser Arg Met Pro Lys Pro Gln Tyr Asp Gly
         260                 265                 270 cat ttg gaa cag att gtt agg ttg gtg ggg gaa gcg aag agg ccg gtt      864
His Leu Glu Gln Ile Val Arg Leu Val Gly Glu Ala Lys Arg Pro Val
         275                 280                 285 ttg tat gtg ggt ggt ggg tgt ttg aat tcg gat gat gag ttg agg cgg      912
Leu Tyr Val Gly Gly Gly Cys Leu Asn Ser Asp Asp Glu Leu Arg Arg
         290                 295                 300 ttt gtg gag ctt acg ggg att ccg gtt gcg agt act ttg atg ggg ctc      960
Phe Val Glu Leu Thr Gly Ile Pro Val Ala Ser Thr Leu Met Gly Leu
305                 310                 315                 320 gga gcg tac cct gct tcg agt gat ttg tcg ctt cat atg ctt ggg atg     1008
Gly Ala Tyr Pro Ala Ser Ser Asp Leu Ser Leu His Met Leu Gly Met
                 325                 330                 335 cat ggt acg gtt tat gcg aat tat gcg gtt gat aag agt gat ttg ttg     1056
His Gly Thr Val Tyr Ala Asn Tyr Ala Val Asp Lys Ser Asp Leu Leu
         340                 345                 350
```

```
ctt gcg ttt ggg gtg cgg ttt gat gat cgt gtg acg ggg aag ctt gag    1104
Leu Ala Phe Gly Val Arg Phe Asp Asp Arg Val Thr Gly Lys Leu Glu
        355                 360                 365 gcg ttt gct agt agg gcg aag att gtt cat att gat att gat cct gct    1152
Ala Phe Ala Ser Arg Ala Lys Ile Val His Ile Asp Ile Asp Pro Ala
370                 375                 380 gaa att ggg aag aat aag cag cct cat gtg tcg att tgt ggt gat att    1200
Glu Ile Gly Lys Asn Lys Gln Pro His Val Ser Ile Cys Gly Asp Ile
385                 390                 395                 400 aag gtc gcg tta cag ggt ttg aac aag att ttg gag gaa aag aat tcg    1248
Lys Val Ala Leu Gln Gly Leu Asn Lys Ile Leu Glu Glu Lys Asn Ser
        405                 410                 415 gtg act aat ctt gat ttt tcg acc tgg aga aag gaa ttg gat gaa caa    1296
Val Thr Asn Leu Asp Phe Ser Thr Trp Arg Lys Glu Leu Asp Glu Gln
        420                 425                 430 aaa atg aag ttc ccg ttg agc ttt aaa acg ttt ggc gaa gcg att cct    1344
Lys Met Lys Phe Pro Leu Ser Phe Lys Thr Phe Gly Glu Ala Ile Pro
        435                 440                 445 cca cag tat gct att caa gtt ctt gat gag tta acg ggc ggg aat gca    1392
Pro Gln Tyr Ala Ile Gln Val Leu Asp Glu Leu Thr Gly Gly Asn Ala
450                 455                 460 att att agc acc ggt gtc ggg caa cat cag atg tgg gct gct cag ttt    1440
Ile Ile Ser Thr Gly Val Gly Gln His Gln Met Trp Ala Ala Gln Phe
465                 470                 475                 480 tac aaa tac aac aaa cct aga caa tgg ctg acg tcg ggc ggg cta ggg    1488
Tyr Lys Tyr Asn Lys Pro Arg Gln Trp Leu Thr Ser Gly Gly Leu Gly
        485                 490                 495 gca atg ggt ttc ggc ctg ccc gct gct atc ggg gcg gcc gtt gca aga    1536
Ala Met Gly Phe Gly Leu Pro Ala Ala Ile Gly Ala Ala Val Ala Arg
        500                 505                 510 cct gat gcg gta gta gtt gac atc gac ggt gac gga agc ttt atg atg    1584
Pro Asp Ala Val Val Val Asp Ile Asp Gly Asp Gly Ser Phe Met Met
        515                 520                 525 aat gtt caa gag tta gcc aca atc cgt gtt gaa aat ctg ccg gtt aag    1632
Asn Val Gln Glu Leu Ala Thr Ile Arg Val Glu Asn Leu Pro Val Lys
530                 535                 540 att tta tta ctt aac aac cag cat ttg ggt atg gtg gtt cag tgg gag    1680
Ile Leu Leu Leu Asn Asn Gln His Leu Gly Met Val Val Gln Trp Glu
545                 550                 555                 560 gat cgg ttt tac aag gcg aat cgg gct cat acc tac tta gga aac ccg    1728
Asp Arg Phe Tyr Lys Ala Asn Arg Ala His Thr Tyr Leu Gly Asn Pro
        565                 570                 575 tca aaa gag tcg gaa ata ttc cct aac atg gtg aag ttt gct gaa gcc    1776
Ser Lys Glu Ser Glu Ile Phe Pro Asn Met Val Lys Phe Ala Glu Ala
        580                 585                 590 tgt gat atc ccg gct gct cga gtg acc caa aag gcg gat cta cga gca    1824
Cys Asp Ile Pro Ala Ala Arg Val Thr Gln Lys Ala Asp Leu Arg Ala
        595                 600                 605 gct att cag aag atg ttg gat aca ccc ggg cct tac ttg ttg gat gtg    1872
Ala Ile Gln Lys Met Leu Asp Thr Pro Gly Pro Tyr Leu Leu Asp Val
610                 615                 620 att gtg ccg cat caa gaa cac gtg ttg ccc atg atc ccg gct ggc gga    1920
Ile Val Pro His Gln Glu His Val Leu Pro Met Ile Pro Ala Gly Gly
625                 630                 635                 640 ggt ttc tcg gat gtg atc acc gag ggt gat ggc aga acg aaa tat tga    1968
Gly Phe Ser Asp Val Ile Thr Glu Gly Asp Gly Arg Thr Lys Tyr *
        645                 650                 655
```

<210> SEQ ID NO 4

<211> LENGTH: 655
<212> TYPE: PRT
<213> ORGANISM: Helianthus annus

<400> SEQUENCE: 4

```
Met Ala Ala Pro Pro Asn Pro Ser Ile Ser Phe Lys Pro Pro Ser Pro
  1               5                  10                  15

Ala Ala Ala Leu Pro Pro Arg Ser Ala Phe Leu Pro Arg Phe Ala Leu
             20                  25                  30

Pro Ile Thr Ser Thr Thr Gln Lys Arg His Arg Leu His Ile Ser Asn
         35                  40                  45

Val Leu Ser Asp Ser Lys Ser Thr Thr Thr Thr Thr Thr Thr Thr Gln
 50                  55                  60

Arg Pro Leu Pro Val Gln Pro Phe Val Ser Arg Tyr Ala Pro Asp Gln
 65                  70                  75                  80

Pro Arg Lys Gly Ala Asp Val Leu Val Glu Ala Leu Glu Arg Glu Gly
                 85                  90                  95

Val Thr Asp Val Phe Ala Tyr Pro Gly Gly Ala Ser Met Glu Ile His
            100                 105                 110

Gln Ala Leu Thr Arg Ser Ser Thr Ile Arg Asn Val Leu Pro Arg His
        115                 120                 125

Glu Gln Gly Gly Val Phe Ala Ala Glu Gly Tyr Ala Arg Ala Ser Gly
    130                 135                 140

Leu Pro Gly Val Cys Ile Ala Thr Ser Gly Pro Gly Ala Thr Asn Leu
145                 150                 155                 160

Val Ser Gly Leu Ala Asp Ala Leu Leu Asp Ser Val Pro Met Val Ala
                165                 170                 175

Ile Thr Gly Gln Val Pro Arg Arg Met Ile Gly Thr Asp Ala Phe Gln
            180                 185                 190

Glu Thr Pro Ile Val Glu Val Thr Arg Ser Ile Thr Lys His Asn Tyr
        195                 200                 205

Leu Val Leu Asp Val Glu Asp Ile Pro Arg Ile Val Arg Glu Ala Phe
    210                 215                 220

Tyr Leu Ala Ser Ser Gly Arg Pro Gly Pro Val Leu Ile Asp Val Pro
225                 230                 235                 240

Lys Asp Ile Gln Gln Gln Leu Val Val Pro Lys Trp Asp Glu Pro Met
                245                 250                 255

Arg Leu Pro Gly Tyr Leu Ser Arg Met Pro Lys Pro Gln Tyr Asp Gly
            260                 265                 270

His Leu Glu Gln Ile Val Arg Leu Val Gly Glu Ala Lys Arg Pro Val
        275                 280                 285

Leu Tyr Val Gly Gly Cys Leu Asn Ser Asp Asp Glu Leu Arg Arg
    290                 295                 300

Phe Val Glu Leu Thr Gly Ile Pro Val Ala Ser Thr Leu Met Gly Leu
305                 310                 315                 320

Gly Ala Tyr Pro Ala Ser Ser Asp Leu Ser Leu His Met Leu Gly Met
                325                 330                 335

His Gly Thr Val Tyr Ala Asn Tyr Ala Val Asp Lys Ser Asp Leu Leu
            340                 345                 350

Leu Ala Phe Gly Val Arg Phe Asp Asp Arg Val Thr Gly Lys Leu Glu
        355                 360                 365

Ala Phe Ala Ser Arg Ala Lys Ile Val His Ile Asp Ile Asp Pro Ala
    370                 375                 380

Glu Ile Gly Lys Asn Lys Gln Pro His Val Ser Ile Cys Gly Asp Ile
```

-continued

```
               385                 390                 395                 400
Lys Val Ala Leu Gln Gly Leu Asn Lys Ile Leu Glu Glu Lys Asn Ser
                405                 410                 415
Val Thr Asn Leu Asp Phe Ser Thr Trp Arg Lys Glu Leu Asp Glu Gln
                420                 425                 430
Lys Met Lys Phe Pro Leu Ser Phe Lys Thr Phe Gly Glu Ala Ile Pro
                435                 440                 445
Pro Gln Tyr Ala Ile Gln Val Leu Asp Glu Leu Thr Gly Gly Asn Ala
                450                 455                 460
Ile Ile Ser Thr Gly Val Gly Gln His Gln Met Trp Ala Ala Gln Phe
465                 470                 475                 480
Tyr Lys Tyr Asn Lys Pro Arg Gln Trp Leu Thr Ser Gly Gly Leu Gly
                485                 490                 495
Ala Met Gly Phe Gly Leu Pro Ala Ala Ile Gly Ala Ala Val Ala Arg
                500                 505                 510
Pro Asp Ala Val Val Asp Ile Asp Gly Asp Gly Ser Phe Met Met
                515                 520                 525
Asn Val Gln Glu Leu Ala Thr Ile Arg Val Glu Asn Leu Pro Val Lys
                530                 535                 540
Ile Leu Leu Leu Asn Asn Gln His Leu Gly Met Val Val Gln Trp Glu
545                 550                 555                 560
Asp Arg Phe Tyr Lys Ala Asn Arg Ala His Thr Tyr Leu Gly Asn Pro
                565                 570                 575
Ser Lys Glu Ser Glu Ile Phe Pro Asn Met Val Lys Phe Ala Glu Ala
                580                 585                 590
Cys Asp Ile Pro Ala Ala Arg Val Thr Gln Lys Ala Asp Leu Arg Ala
                595                 600                 605
Ala Ile Gln Lys Met Leu Asp Thr Pro Gly Pro Tyr Leu Leu Asp Val
                610                 615                 620
Ile Val Pro His Gln Glu His Val Leu Pro Met Ile Pro Ala Gly Gly
625                 630                 635                 640
Gly Phe Ser Asp Val Ile Thr Glu Gly Asp Gly Arg Thr Lys Tyr
                645                 650                 655

<210> SEQ ID NO 5
<211> LENGTH: 1716
<212> TYPE: DNA
<213> ORGANISM: Helianthus annus
<220> FEATURE:
<221> NAME/KEY: CDS
<222> LOCATION: (1)...(1716)

<400> SEQUENCE: 5 gca gac gtg ttg gtg gaa gct ctg gaa cgg gaa ggt gtc acc gac gtc      48
Ala Asp Val Leu Val Glu Ala Leu Glu Arg Glu Gly Val Thr Asp Val
 1               5                  10                  15 ttc gcc tac ccc ggc ggc gcg tca atg gag atc cac caa gct ctc acg      96
Phe Ala Tyr Pro Gly Gly Ala Ser Met Glu Ile His Gln Ala Leu Thr
             20                  25                  30 cgc tca agc act atc cgc aat gtg ctc ccc cgt cac gaa cag ggc ggc     144
Arg Ser Ser Thr Ile Arg Asn Val Leu Pro Arg His Glu Gln Gly Gly
         35                  40                  45 gtg ttc gcc gcc gaa ggc tac gcg cgc gcc tcc ggt ctt ccc ggc gtg     192
Val Phe Ala Ala Glu Gly Tyr Ala Arg Ala Ser Gly Leu Pro Gly Val
     50                  55                  60 tgt atc gcc act tcc ggt ccc gga gct acg aac cta gtt agt ggt ctt     240
Cys Ile Ala Thr Ser Gly Pro Gly Ala Thr Asn Leu Val Ser Gly Leu
 65                  70                  75                  80
```

|    |    |    |    |    |    |    |    |    |    |    |    |    |    |    |    |      |
|----|----|----|----|----|----|----|----|----|----|----|----|----|----|----|----|------|
| gct | gac | gcg | ctg | tta | gac | agt | gtc | ccc | atg | gtg | gca | atc | acc | ggt | caa | 288  |
| Ala | Asp | Ala | Leu | Leu | Asp | Ser | Val | Pro | Met | Val | Ala | Ile | Thr | Gly | Gln |      |
|     |     |     |     | 85  |     |     |     |     | 90  |     |     |     |     | 95  |     |      |
| gtt | ctc | cgg | aga | atg | atc | gga | acc | gat | gcg | ttt | caa | gaa | acc | cca | att | 336  |
| Val | Leu | Arg | Arg | Met | Ile | Gly | Thr | Asp | Ala | Phe | Gln | Glu | Thr | Pro | Ile |      |
|     |     |     | 100 |     |     |     |     | 105 |     |     |     |     | 110 |     |     |      |
| gtt | gag | gta | aca | cgt | tcg | atc | act | aaa | cat | aat | tat | ctt | gtg | ttg | gat | 384  |
| Val | Glu | Val | Thr | Arg | Ser | Ile | Thr | Lys | His | Asn | Tyr | Leu | Val | Leu | Asp |      |
|     |     |     | 115 |     |     |     |     | 120 |     |     |     |     | 125 |     |     |      |
| gtt | gag | gat | att | ccc | aga | att | gtt | cgt | gag | gct | ttt | tat | ctt | gcg | agt | 432  |
| Val | Glu | Asp | Ile | Pro | Arg | Ile | Val | Arg | Glu | Ala | Phe | Tyr | Leu | Ala | Ser |      |
|     | 130 |     |     |     |     | 135 |     |     |     |     | 140 |     |     |     |     |      |
| tcg | ggt | cga | ccc | ggc | ccg | gtt | ttg | ata | gat | gta | ccg | aaa | gat | ata | cag | 480  |
| Ser | Gly | Arg | Pro | Gly | Pro | Val | Leu | Ile | Asp | Val | Pro | Lys | Asp | Ile | Gln |      |
| 145 |     |     |     |     | 150 |     |     |     |     | 155 |     |     |     |     | 160 |      |
| caa | cag | tta | gtg | gtg | ccg | aaa | tgg | gat | gaa | ccg | atg | agg | tta | ccg | ggt | 528  |
| Gln | Gln | Leu | Val | Val | Pro | Lys | Trp | Asp | Glu | Pro | Met | Arg | Leu | Pro | Gly |      |
|     |     |     |     | 165 |     |     |     |     | 170 |     |     |     |     | 175 |     |      |
| tat | ttg | tct | aga | atg | ccg | aag | cct | caa | tat | gat | ggg | cat | ttg | gaa | cag | 576  |
| Tyr | Leu | Ser | Arg | Met | Pro | Lys | Pro | Gln | Tyr | Asp | Gly | His | Leu | Glu | Gln |      |
|     |     |     | 180 |     |     |     |     | 185 |     |     |     |     | 190 |     |     |      |
| att | gtt | agg | ttg | gtg | ggg | gaa | gcg | aag | agg | ccg | gtt | ttg | tat | gtg | ggt | 624  |
| Ile | Val | Arg | Leu | Val | Gly | Glu | Ala | Lys | Arg | Pro | Val | Leu | Tyr | Val | Gly |      |
|     |     | 195 |     |     |     |     | 200 |     |     |     |     | 205 |     |     |     |      |
| ggt | ggg | tgt | ttg | aat | tcg | gat | gat | gag | ttg | agg | cgg | ttt | gtg | gag | ctt | 672  |
| Gly | Gly | Cys | Leu | Asn | Ser | Asp | Asp | Glu | Leu | Arg | Arg | Phe | Val | Glu | Leu |      |
|     | 210 |     |     |     |     | 215 |     |     |     |     | 220 |     |     |     |     |      |
| acg | ggg | att | ccg | gtt | gcg | agt | act | ttg | atg | ggg | ctc | gga | gcg | tac | cct | 720  |
| Thr | Gly | Ile | Pro | Val | Ala | Ser | Thr | Leu | Met | Gly | Leu | Gly | Ala | Tyr | Pro |      |
| 225 |     |     |     |     | 230 |     |     |     |     | 235 |     |     |     |     | 240 |      |
| gct | tcg | agt | gat | ttg | tcg | ctt | cat | atg | ctt | ggg | atg | cat | ggt | acg | gtt | 768  |
| Ala | Ser | Ser | Asp | Leu | Ser | Leu | His | Met | Leu | Gly | Met | His | Gly | Thr | Val |      |
|     |     |     |     | 245 |     |     |     |     | 250 |     |     |     |     | 255 |     |      |
| tat | gcg | aat | tat | gcg | gtt | gat | aag | agt | gat | ttg | ttg | ctt | gcg | ttt | ggg | 816  |
| Tyr | Ala | Asn | Tyr | Ala | Val | Asp | Lys | Ser | Asp | Leu | Leu | Leu | Ala | Phe | Gly |      |
|     |     | 260 |     |     |     |     | 265 |     |     |     |     | 270 |     |     |     |      |
| gtg | cgg | ttt | gat | gat | cgt | gtg | acg | ggg | aag | ctt | gag | gcg | ttt | gct | agt | 864  |
| Val | Arg | Phe | Asp | Asp | Arg | Val | Thr | Gly | Lys | Leu | Glu | Ala | Phe | Ala | Ser |      |
|     | 275 |     |     |     |     | 280 |     |     |     |     | 285 |     |     |     |     |      |
| agg | gcg | aag | att | gtt | cat | att | gat | att | gat | cct | gct | gaa | att | ggg | aag | 912  |
| Arg | Ala | Lys | Ile | Val | His | Ile | Asp | Ile | Asp | Pro | Ala | Glu | Ile | Gly | Lys |      |
| 290 |     |     |     |     | 295 |     |     |     |     | 300 |     |     |     |     |     |      |
| aat | aag | cag | cct | cat | gtg | tcg | att | tgt | ggt | gat | att | aag | gtc | gcg | tta | 960  |
| Asn | Lys | Gln | Pro | His | Val | Ser | Ile | Cys | Gly | Asp | Ile | Lys | Val | Ala | Leu |      |
| 305 |     |     |     |     | 310 |     |     |     |     | 315 |     |     |     |     | 320 |      |
| cag | ggt | ttg | aac | aag | att | ttg | gag | gaa | aag | aat | tcg | gtg | act | aat | ctt | 1008 |
| Gln | Gly | Leu | Asn | Lys | Ile | Leu | Glu | Glu | Lys | Asn | Ser | Val | Thr | Asn | Leu |      |
|     |     |     |     | 325 |     |     |     |     | 330 |     |     |     |     | 335 |     |      |
| gat | ttt | tcg | acc | tgg | aga | aag | gaa | ttg | gat | gaa | caa | aaa | atg | aag | ttc | 1056 |
| Asp | Phe | Ser | Thr | Trp | Arg | Lys | Glu | Leu | Asp | Glu | Gln | Lys | Met | Lys | Phe |      |
|     |     |     | 340 |     |     |     |     | 345 |     |     |     |     | 350 |     |     |      |
| ccg | ttg | agc | ttt | aaa | acg | ttt | ggc | gaa | gcg | att | cct | cca | cag | tat | gct | 1104 |
| Pro | Leu | Ser | Phe | Lys | Thr | Phe | Gly | Glu | Ala | Ile | Pro | Pro | Gln | Tyr | Ala |      |
|     |     | 355 |     |     |     |     | 360 |     |     |     |     | 365 |     |     |     |      |
| att | caa | gtt | ctt | gat | gag | tta | acg | ggc | ggg | aat | gca | att | att | agc | acc | 1152 |
| Ile | Gln | Val | Leu | Asp | Glu | Leu | Thr | Gly | Gly | Asn | Ala | Ile | Ile | Ser | Thr |      |
| 370 |     |     |     |     | 375 |     |     |     |     | 380 |     |     |     |     |     |      |
| ggt | gtc | ggg | caa | cat | cag | atg | tgg | gct | gct | cag | ttt | tac | aaa | tac | aac | 1200 |

```
Gly Val Gly Gln His Gln Met Trp Ala Ala Gln Phe Tyr Lys Tyr Asn
385                 390                 395                 400 aaa cct aga caa tgg ctg acg tcg ggc ggg cta ggg gca atg ggt ttc    1248
Lys Pro Arg Gln Trp Leu Thr Ser Gly Gly Leu Gly Ala Met Gly Phe
                405                 410                 415 ggc ctg ccc gct gct atc ggg gcg gcc gtt gca aga cct gat gcg gta    1296
Gly Leu Pro Ala Ala Ile Gly Ala Ala Val Ala Arg Pro Asp Ala Val
            420                 425                 430 gta gtt gac atc gac ggt gac gga agc ttt atg atg aat gtt caa gag    1344
Val Val Asp Ile Asp Gly Asp Gly Ser Phe Met Met Asn Val Gln Glu
        435                 440                 445 tta gcc aca atc cgt gtt gaa aat ctg ccg gtt aag att tta tta ctt    1392
Leu Ala Thr Ile Arg Val Glu Asn Leu Pro Val Lys Ile Leu Leu Leu
    450                 455                 460 aac aac cag cat ttg ggt atg gtg gtt cag tgg gag gat cgg ttt tac    1440
Asn Asn Gln His Leu Gly Met Val Val Gln Trp Glu Asp Arg Phe Tyr
465                 470                 475                 480 aag gcg aat cgg gct cat acc tac tta gga aac ccg tca aaa gag tcg    1488
Lys Ala Asn Arg Ala His Thr Tyr Leu Gly Asn Pro Ser Lys Glu Ser
                485                 490                 495 gaa ata ttc cct aac atg gtg aag ttt gct gaa gcc tgt gat atc ccg    1536
Glu Ile Phe Pro Asn Met Val Lys Phe Ala Glu Ala Cys Asp Ile Pro
            500                 505                 510 gct gct cga gtg acc caa aag gcg gat cta cga gca gct att cag aag    1584
Ala Ala Arg Val Thr Gln Lys Ala Asp Leu Arg Ala Ala Ile Gln Lys
        515                 520                 525 atg ttg gat aca ccc ggg cct tac ttg ttg gat gtg att gtg ccg cat    1632
Met Leu Asp Thr Pro Gly Pro Tyr Leu Leu Asp Val Ile Val Pro His
    530                 535                 540 caa gaa cac gtg ttg ccc atg atc ccg gct ggc gga ggt ttc tcg gat    1680
Gln Glu His Val Leu Pro Met Ile Pro Ala Gly Gly Gly Phe Ser Asp
545                 550                 555                 560 gtg atc acc gag ggt gat ggc aga acg aaa tat tga                    1716
Val Ile Thr Glu Gly Asp Gly Arg Thr Lys Tyr  *
                565                 570

<210> SEQ ID NO 6
<211> LENGTH: 571
<212> TYPE: PRT
<213> ORGANISM: Helianthus annus

<400> SEQUENCE: 6

Ala Asp Val Leu Val Glu Ala Leu Glu Arg Glu Gly Val Thr Asp Val
1               5                   10                  15

Phe Ala Tyr Pro Gly Gly Ala Ser Met Glu Ile His Gln Ala Leu Thr
                20                  25                  30

Arg Ser Ser Thr Ile Arg Asn Val Leu Pro Arg His Glu Gln Gly Gly
            35                  40                  45

Val Phe Ala Ala Glu Gly Tyr Ala Arg Ala Ser Gly Leu Pro Gly Val
        50                  55                  60

Cys Ile Ala Thr Ser Gly Pro Gly Ala Thr Asn Leu Val Ser Gly Leu
65                  70                  75                  80

Ala Asp Ala Leu Leu Asp Ser Val Pro Met Val Ala Ile Thr Gly Gln
                85                  90                  95

Val Leu Arg Arg Met Ile Gly Thr Asp Ala Phe Gln Glu Thr Pro Ile
            100                 105                 110

Val Glu Val Thr Arg Ser Ile Thr Lys His Asn Tyr Leu Val Leu Asp
        115                 120                 125
```

```
Val Glu Asp Ile Pro Arg Ile Val Arg Glu Ala Phe Tyr Leu Ala Ser
130                 135                 140

Ser Gly Arg Pro Gly Pro Val Leu Ile Asp Val Pro Lys Asp Ile Gln
145                 150                 155                 160

Gln Gln Leu Val Val Pro Lys Trp Asp Glu Pro Met Arg Leu Pro Gly
                165                 170                 175

Tyr Leu Ser Arg Met Pro Lys Pro Gln Tyr Asp Gly His Leu Glu Gln
            180                 185                 190

Ile Val Arg Leu Val Gly Glu Ala Lys Arg Pro Val Leu Tyr Val Gly
        195                 200                 205

Gly Gly Cys Leu Asn Ser Asp Asp Glu Leu Arg Arg Phe Val Glu Leu
    210                 215                 220

Thr Gly Ile Pro Val Ala Ser Thr Leu Met Gly Leu Gly Ala Tyr Pro
225                 230                 235                 240

Ala Ser Ser Asp Leu Ser Leu His Met Leu Gly Met His Gly Thr Val
                245                 250                 255

Tyr Ala Asn Tyr Ala Val Asp Lys Ser Asp Leu Leu Leu Ala Phe Gly
            260                 265                 270

Val Arg Phe Asp Asp Arg Val Thr Gly Lys Leu Glu Ala Phe Ala Ser
        275                 280                 285

Arg Ala Lys Ile Val His Ile Asp Ile Asp Pro Ala Glu Ile Gly Lys
290                 295                 300

Asn Lys Gln Pro His Val Ser Ile Cys Gly Asp Ile Lys Val Ala Leu
305                 310                 315                 320

Gln Gly Leu Asn Lys Ile Leu Glu Glu Lys Asn Ser Val Thr Asn Leu
                325                 330                 335

Asp Phe Ser Thr Trp Arg Lys Glu Leu Asp Glu Gln Lys Met Lys Phe
            340                 345                 350

Pro Leu Ser Phe Lys Thr Phe Gly Glu Ala Ile Pro Pro Gln Tyr Ala
        355                 360                 365

Ile Gln Val Leu Asp Glu Leu Thr Gly Gly Asn Ala Ile Ile Ser Thr
    370                 375                 380

Gly Val Gly Gln His Gln Met Trp Ala Ala Gln Phe Tyr Lys Tyr Asn
385                 390                 395                 400

Lys Pro Arg Gln Trp Leu Thr Ser Gly Gly Leu Gly Ala Met Gly Phe
                405                 410                 415

Gly Leu Pro Ala Ala Ile Gly Ala Ala Val Ala Arg Pro Asp Ala Val
            420                 425                 430

Val Val Asp Ile Asp Gly Asp Gly Ser Phe Met Met Asn Val Gln Glu
        435                 440                 445

Leu Ala Thr Ile Arg Val Glu Asn Leu Pro Val Lys Ile Leu Leu Leu
450                 455                 460

Asn Asn Gln His Leu Gly Met Val Val Gln Trp Glu Asp Arg Phe Tyr
465                 470                 475                 480

Lys Ala Asn Arg Ala His Thr Tyr Leu Gly Asn Pro Ser Lys Glu Ser
                485                 490                 495

Glu Ile Phe Pro Asn Met Val Lys Phe Ala Glu Ala Cys Asp Ile Pro
            500                 505                 510

Ala Ala Arg Val Thr Gln Lys Ala Asp Leu Arg Ala Ala Ile Gln Lys
        515                 520                 525

Met Leu Asp Thr Pro Gly Pro Tyr Leu Leu Asp Val Ile Val Pro His
530                 535                 540

Gln Glu His Val Leu Pro Met Ile Pro Ala Gly Gly Gly Phe Ser Asp
```

```
                                 545                 550                 555                 560
                        Val Ile Thr Glu Gly Asp Gly Arg Thr Lys Tyr
                                        565                 570

<210> SEQ ID NO 7
<211> LENGTH: 1716
<212> TYPE: DNA
<213> ORGANISM: Helianthus annus
<220> FEATURE:
<221> NAME/KEY: CDS
<222> LOCATION: (1)...(1716)

<400> SEQUENCE: 7 gca gac gtg ttg gtg gaa gct ctg gaa cgg gaa ggt gtc acc gac gtc      48
Ala Asp Val Leu Val Glu Ala Leu Glu Arg Glu Gly Val Thr Asp Val
 1               5                  10                  15 ttc gcc tac ccc ggc ggc gcg tca atg gag atc cac caa gct ctc acg      96
Phe Ala Tyr Pro Gly Gly Ala Ser Met Glu Ile His Gln Ala Leu Thr
             20                  25                  30 cgc tca agc act atc cgc aat gtg ctc ccc cgt cac gaa cag ggc ggc     144
Arg Ser Ser Thr Ile Arg Asn Val Leu Pro Arg His Glu Gln Gly Gly
         35                  40                  45 gtg ttc gcc gcc gaa ggc tac gcg cgc gcc tcc ggt ctt ccc ggc gtg     192
Val Phe Ala Ala Glu Gly Tyr Ala Arg Ala Ser Gly Leu Pro Gly Val
     50                  55                  60 tgt atc gcc act tcc ggt ccc gga gct acg aac cta gtt agt ggt ctt     240
Cys Ile Ala Thr Ser Gly Pro Gly Ala Thr Asn Leu Val Ser Gly Leu
 65                  70                  75                  80 gct gac gcg ctg tta gac agt gtc ccc atg gtg gca atc acc ggt caa     288
Ala Asp Ala Leu Leu Asp Ser Val Pro Met Val Ala Ile Thr Gly Gln
                 85                  90                  95 gtt ccc cgg aga atg atc gga acc gat gcg ttt caa gaa acc cca att     336
Val Pro Arg Arg Met Ile Gly Thr Asp Ala Phe Gln Glu Thr Pro Ile
            100                 105                 110 gtt gag gta aca cgt tcg atc act aaa cat aat tat ctt gtg ttg gat     384
Val Glu Val Thr Arg Ser Ile Thr Lys His Asn Tyr Leu Val Leu Asp
        115                 120                 125 gtt gag gat att ccc aga att gtt cgt gag gct ttt tat ctt gcg agt     432
Val Glu Asp Ile Pro Arg Ile Val Arg Glu Ala Phe Tyr Leu Ala Ser
    130                 135                 140 tcg ggt cga ccc ggc ccg gtt ttg ata gat gta ccg aaa gat ata cag     480
Ser Gly Arg Pro Gly Pro Val Leu Ile Asp Val Pro Lys Asp Ile Gln
145                 150                 155                 160 caa cag tta gtg gtg ccg aaa tgg gat gaa ccg atg agg tta ccg ggt     528
Gln Gln Leu Val Val Pro Lys Trp Asp Glu Pro Met Arg Leu Pro Gly
                165                 170                 175 tat ttg tct aga atg ccg aag cct caa tat gat ggg cat ttg gaa cag     576
Tyr Leu Ser Arg Met Pro Lys Pro Gln Tyr Asp Gly His Leu Glu Gln
            180                 185                 190 att gtt agg ttg gtg ggg gaa gcg aag agg ccg gtt ttg tat gtg ggt     624
Ile Val Arg Leu Val Gly Glu Ala Lys Arg Pro Val Leu Tyr Val Gly
        195                 200                 205 ggt ggg tgt ttg aat tcg gat gat gag ttg agg cgg ttt gtg gag ctt     672
Gly Gly Cys Leu Asn Ser Asp Asp Glu Leu Arg Arg Phe Val Glu Leu
    210                 215                 220 acg ggg att ccg gtt gcg agt act ttg atg ggg ctc gga gcg tac cct     720
Thr Gly Ile Pro Val Ala Ser Thr Leu Met Gly Leu Gly Ala Tyr Pro
225                 230                 235                 240 gct tcg agt gat ttg tcg ctt cat atg ctt ggg atg cat ggt acg gtt     768
Ala Ser Ser Asp Leu Ser Leu His Met Leu Gly Met His Gly Thr Val
                245                 250                 255
```

```
                                                                      -continued tat gcg aat tat gcg gtt gat aag agt gat ttg ttg ctt gcg ttt ggg        816
Tyr Ala Asn Tyr Ala Val Asp Lys Ser Asp Leu Leu Leu Ala Phe Gly
            260                 265                 270 gtg cgg ttt gat gat cgt gtg acg ggg aag ctt gag gcg ttt gct agt        864
Val Arg Phe Asp Asp Arg Val Thr Gly Lys Leu Glu Ala Phe Ala Ser
        275                 280                 285 agg gcg aag att gtt cat att gat att gat cct gct gaa att ggg aag        912
Arg Ala Lys Ile Val His Ile Asp Ile Asp Pro Ala Glu Ile Gly Lys
    290                 295                 300 aat aag cag cct cat gtg tcg att tgt ggt gat att aag gtc gcg tta        960
Asn Lys Gln Pro His Val Ser Ile Cys Gly Asp Ile Lys Val Ala Leu
305                 310                 315                 320 cag ggt ttg aac aag att ttg gag gaa aag aat tcg gtg act aat ctt       1008
Gln Gly Leu Asn Lys Ile Leu Glu Glu Lys Asn Ser Val Thr Asn Leu
                325                 330                 335 gat ttt tcg acc tgg aga aag gaa ttg gat gaa caa aaa atg aag ttc       1056
Asp Phe Ser Thr Trp Arg Lys Glu Leu Asp Glu Gln Lys Met Lys Phe
            340                 345                 350 ccg ttg agc ttt aaa acg ttt ggc gaa gcg att cct cca cag tat gct       1104
Pro Leu Ser Phe Lys Thr Phe Gly Glu Ala Ile Pro Pro Gln Tyr Ala
        355                 360                 365 att caa gtt ctt gat gag tta acg ggc ggg aat gca att att agc acc       1152
Ile Gln Val Leu Asp Glu Leu Thr Gly Gly Asn Ala Ile Ile Ser Thr
    370                 375                 380 ggt gtc ggg caa cat cag atg tgg gct gct cag ttt tac aaa tac aac       1200
Gly Val Gly Gln His Gln Met Trp Ala Ala Gln Phe Tyr Lys Tyr Asn
385                 390                 395                 400 aaa cct aga caa tgg ctg acg tcg ggc ggg cta ggg gca atg ggt ttc       1248
Lys Pro Arg Gln Trp Leu Thr Ser Gly Gly Leu Gly Ala Met Gly Phe
                405                 410                 415 ggc ctg ccc gct gct atc ggg gcg gcc gtt gca aga cct gat gcg gta       1296
Gly Leu Pro Ala Ala Ile Gly Ala Ala Val Ala Arg Pro Asp Ala Val
            420                 425                 430 gta gtt gac atc gac ggt gac gga agc ttt atg atg aat gtt caa gag       1344
Val Val Asp Ile Asp Gly Asp Gly Ser Phe Met Met Asn Val Gln Glu
        435                 440                 445 tta gcc aca atc cgt gtt gaa aat ctg ccg gtt aag att tta tta ctt       1392
Leu Ala Thr Ile Arg Val Glu Asn Leu Pro Val Lys Ile Leu Leu Leu
    450                 455                 460 aac aac cag cat ttg ggt atg gtg gtt cag tgg gag gat cgg ttt tac       1440
Asn Asn Gln His Leu Gly Met Val Val Gln Trp Glu Asp Arg Phe Tyr
465                 470                 475                 480 aag gcg aat cgg gct cat acc tac tta gga aac ccg tca aaa gag tcg       1488
Lys Ala Asn Arg Ala His Thr Tyr Leu Gly Asn Pro Ser Lys Glu Ser
                485                 490                 495 gaa ata ttc cct aac atg gtg aag ttt gct gaa gcc tgt gat atc ccg       1536
Glu Ile Phe Pro Asn Met Val Lys Phe Ala Glu Ala Cys Asp Ile Pro
            500                 505                 510 gct gct cga gtg acc caa aag gcg gat cta cga gca gct att cag aag       1584
Ala Ala Arg Val Thr Gln Lys Ala Asp Leu Arg Ala Ala Ile Gln Lys
        515                 520                 525 atg ttg gat aca ccc ggg cct tac ttg ttg gat gtg att gtg ccg cat       1632
Met Leu Asp Thr Pro Gly Pro Tyr Leu Leu Asp Val Ile Val Pro His
    530                 535                 540 caa gaa cac gtg ttg ccc atg atc ccg gct ggc gga ggt ttc tcg gat       1680
Gln Glu His Val Leu Pro Met Ile Pro Ala Gly Gly Gly Phe Ser Asp
545                 550                 555                 560 gtg atc acc gag ggt gat ggc aga acg aaa tat tga                       1716
Val Ile Thr Glu Gly Asp Gly Arg Thr Lys Tyr  *
```

-continued

```
                565                 570

<210> SEQ ID NO 8
<211> LENGTH: 571
<212> TYPE: PRT
<213> ORGANISM: Helianthus annus

<400> SEQUENCE: 8

Ala Asp Val Leu Val Glu Ala Leu Glu Arg Glu Gly Val Thr Asp Val
 1               5                  10                  15

Phe Ala Tyr Pro Gly Gly Ala Ser Met Glu Ile His Gln Ala Leu Thr
             20                  25                  30

Arg Ser Ser Thr Ile Arg Asn Val Leu Pro Arg His Glu Gln Gly Gly
         35                  40                  45

Val Phe Ala Ala Glu Gly Tyr Ala Arg Ala Ser Gly Leu Pro Gly Val
     50                  55                  60

Cys Ile Ala Thr Ser Gly Pro Gly Ala Thr Asn Leu Val Ser Gly Leu
 65                  70                  75                  80

Ala Asp Ala Leu Leu Asp Ser Val Pro Met Val Ala Ile Thr Gly Gln
                 85                  90                  95

Val Pro Arg Arg Met Ile Gly Thr Asp Ala Phe Gln Glu Thr Pro Ile
            100                 105                 110

Val Glu Val Thr Arg Ser Ile Thr Lys His Asn Tyr Leu Val Leu Asp
        115                 120                 125

Val Glu Asp Ile Pro Arg Ile Val Arg Glu Ala Phe Tyr Leu Ala Ser
    130                 135                 140

Ser Gly Arg Pro Gly Pro Val Leu Ile Asp Val Pro Lys Asp Ile Gln
145                 150                 155                 160

Gln Gln Leu Val Val Pro Lys Trp Asp Glu Pro Met Arg Leu Pro Gly
                165                 170                 175

Tyr Leu Ser Arg Met Pro Lys Pro Gln Tyr Asp Gly His Leu Glu Gln
            180                 185                 190

Ile Val Arg Leu Val Gly Glu Ala Lys Arg Pro Val Leu Tyr Val Gly
        195                 200                 205

Gly Gly Cys Leu Asn Ser Asp Asp Glu Leu Arg Arg Phe Val Glu Leu
    210                 215                 220

Thr Gly Ile Pro Val Ala Ser Thr Leu Met Gly Leu Gly Ala Tyr Pro
225                 230                 235                 240

Ala Ser Ser Asp Leu Ser Leu His Met Leu Gly Met His Gly Thr Val
                245                 250                 255

Tyr Ala Asn Tyr Ala Val Asp Lys Ser Asp Leu Leu Leu Ala Phe Gly
            260                 265                 270

Val Arg Phe Asp Asp Arg Val Thr Gly Lys Leu Glu Ala Phe Ala Ser
        275                 280                 285

Arg Ala Lys Ile Val His Ile Asp Ile Asp Pro Ala Glu Ile Gly Lys
    290                 295                 300

Asn Lys Gln Pro His Val Ser Ile Cys Gly Asp Ile Lys Val Ala Leu
305                 310                 315                 320

Gln Gly Leu Asn Lys Ile Leu Glu Glu Lys Asn Ser Val Thr Asn Leu
                325                 330                 335

Asp Phe Ser Thr Trp Arg Lys Glu Leu Asp Glu Gln Lys Met Lys Phe
            340                 345                 350

Pro Leu Ser Phe Lys Thr Phe Gly Glu Ala Ile Pro Pro Gln Tyr Ala
        355                 360                 365
```

-continued

```
Ile Gln Val Leu Asp Glu Leu Thr Gly Gly Asn Ala Ile Ile Ser Thr
    370                 375                 380
Gly Val Gly Gln His Gln Met Trp Ala Ala Gln Phe Tyr Lys Tyr Asn
385                 390                 395                 400
Lys Pro Arg Gln Trp Leu Thr Ser Gly Leu Gly Ala Met Gly Phe
                405                 410                 415
Gly Leu Pro Ala Ala Ile Gly Ala Ala Val Ala Arg Pro Asp Ala Val
                420                 425                 430
Val Val Asp Ile Asp Gly Asp Gly Ser Phe Met Met Asn Val Gln Glu
                435                 440                 445
Leu Ala Thr Ile Arg Val Glu Asn Leu Pro Val Lys Ile Leu Leu Leu
    450                 455                 460
Asn Asn Gln His Leu Gly Met Val Val Gln Trp Glu Asp Arg Phe Tyr
465                 470                 475                 480
Lys Ala Asn Arg Ala His Thr Tyr Leu Gly Asn Pro Ser Lys Glu Ser
                485                 490                 495
Glu Ile Phe Pro Asn Met Val Lys Phe Ala Glu Ala Cys Asp Ile Pro
                500                 505                 510
Ala Ala Arg Val Thr Gln Lys Ala Asp Leu Arg Ala Ala Ile Gln Lys
                515                 520                 525
Met Leu Asp Thr Pro Gly Pro Tyr Leu Leu Asp Val Ile Val Pro His
    530                 535                 540
Gln Glu His Val Leu Pro Met Ile Pro Ala Gly Gly Phe Ser Asp
545                 550                 555                 560
Val Ile Thr Glu Gly Asp Gly Arg Thr Lys Tyr
                565                 570

<210> SEQ ID NO 9
<211> LENGTH: 1947
<212> TYPE: DNA
<213> ORGANISM: Xanthium sp.
<220> FEATURE:
<221> NAME/KEY: CDS
<222> LOCATION: (1)...(1947)

<400> SEQUENCE: 9 atg gcg gcc atc cct cat aca aac cct tcc atc acc acc aaa cca ccc      48
Met Ala Ala Ile Pro His Thr Asn Pro Ser Ile Thr Thr Lys Pro Pro
1               5                   10                  15 tca tct cca cca cgt ccc acc ttc ctc gcc cgt ttc aca ttc cca ata      96
Ser Ser Pro Pro Arg Pro Thr Phe Leu Ala Arg Phe Thr Phe Pro Ile
                20                  25                  30 acc tcc act tcc cat aaa cga cac cgt ctc cac atc tcc aac gtc ctc     144
Thr Ser Thr Ser His Lys Arg His Arg Leu His Ile Ser Asn Val Leu
            35                  40                  45 tcc gac tcc aaa ccc acc atc acc cat tca cca tta cca acc gaa tca     192
Ser Asp Ser Lys Pro Thr Ile Thr His Ser Pro Leu Pro Thr Glu Ser
    50                  55                  60 ttt atc tcc cgt tac gct cca gac caa cca aga aaa ggc gct gat gtt     240
Phe Ile Ser Arg Tyr Ala Pro Asp Gln Pro Arg Lys Gly Ala Asp Val
65                  70                  75                  80 ctc gtc gaa gct ctg gaa cgt gaa ggc gtt aca gac gtc ttc gct tac     288
Leu Val Glu Ala Leu Glu Arg Glu Gly Val Thr Asp Val Phe Ala Tyr
                85                  90                  95 cca ggt ggt gcc tcc atg gag atc cac caa gct ctc acg cgc tca acc     336
Pro Gly Gly Ala Ser Met Glu Ile His Gln Ala Leu Thr Arg Ser Thr
                100                 105                 110 acc atc cgc aac gtt ctc cca cgt cac gaa cag ggc ggc gtc ttt gct     384
```

```
Thr Ile Arg Asn Val Leu Pro Arg His Glu Gln Gly Gly Val Phe Ala
        115                 120                 125 gcc gaa ggc tac gca cgt gcc tcc ggt ctt ccc ggc gtc tgt att gca        432
Ala Glu Gly Tyr Ala Arg Ala Ser Gly Leu Pro Gly Val Cys Ile Ala
130                 135                 140 acc tct ggt cct gga gct acg aac cta gta agt ggt ctt gct gat gct        480
Thr Ser Gly Pro Gly Ala Thr Asn Leu Val Ser Gly Leu Ala Asp Ala
145                 150                 155                 160 tta tta gac agt gtt cca atg gtt gct att act ggt caa gtt ccc agg        528
Leu Leu Asp Ser Val Pro Met Val Ala Ile Thr Gly Gln Val Pro Arg
                165                 170                 175 aga atg att gga aca gat gcg ttt caa gaa acc cct att gtt gag gta        576
Arg Met Ile Gly Thr Asp Ala Phe Gln Glu Thr Pro Ile Val Glu Val
            180                 185                 190 aca cgt tcc att act aag cat aat tat tta gtt ttg gat gtc gag gat        624
Thr Arg Ser Ile Thr Lys His Asn Tyr Leu Val Leu Asp Val Glu Asp
        195                 200                 205 att ccc agg att gtt agg gaa gct ttt tat ctt gcg tct tct ggt cga        672
Ile Pro Arg Ile Val Arg Glu Ala Phe Tyr Leu Ala Ser Ser Gly Arg
    210                 215                 220 ccc gga ccg gtt tta att gat gta cct aag gat ata cag cag cag ttg        720
Pro Gly Pro Val Leu Ile Asp Val Pro Lys Asp Ile Gln Gln Gln Leu
225                 230                 235                 240 gta gtg cct aaa tgg gat gag cct att agg tta cct ggg tat ttg tct        768
Val Val Pro Lys Trp Asp Glu Pro Ile Arg Leu Pro Gly Tyr Leu Ser
                245                 250                 255 agg ttg cct aaa acg gag aat aat ggg cag ttg gaa cac att gtt agg        816
Arg Leu Pro Lys Thr Glu Asn Asn Gly Gln Leu Glu His Ile Val Arg
            260                 265                 270 ttg gtg agt gag gcc aag agg ccg gtt ttg tat gtg ggg ggt ggg tgt        864
Leu Val Ser Glu Ala Lys Arg Pro Val Leu Tyr Val Gly Gly Gly Cys
        275                 280                 285 ttg aat tcg gga gat gag ttg agg cgg ttt gtg gag ctt acg ggg ata        912
Leu Asn Ser Gly Asp Glu Leu Arg Arg Phe Val Glu Leu Thr Gly Ile
    290                 295                 300 ccg gtt gcg agt acg ttg atg ggg ctt gga gcg tac cct gct tct agt        960
Pro Val Ala Ser Thr Leu Met Gly Leu Gly Ala Tyr Pro Ala Ser Ser
305                 310                 315                 320 gat ttg tcg ctg cat atg ctt ggg atg cat ggg acg gtt tat gcg aat       1008
Asp Leu Ser Leu His Met Leu Gly Met His Gly Thr Val Tyr Ala Asn
                325                 330                 335 tat gcg gtt gat aag agt gat ttg ttg ctt gcg ttt ggg gta agg ttt       1056
Tyr Ala Val Asp Lys Ser Asp Leu Leu Leu Ala Phe Gly Val Arg Phe
            340                 345                 350 gat gac cgt gtg acg ggg aag ctt gag gct ttt gct agc aga gct aag       1104
Asp Asp Arg Val Thr Gly Lys Leu Glu Ala Phe Ala Ser Arg Ala Lys
        355                 360                 365 att gtt cat att gat att gat tct gcg gaa att ggg aag aat aag cag       1152
Ile Val His Ile Asp Ile Asp Ser Ala Glu Ile Gly Lys Asn Lys Gln
    370                 375                 380 cct cat gtg tcg att tgt ggt gat atc aag gtc gcg tta cag ggt ctg       1200
Pro His Val Ser Ile Cys Gly Asp Ile Lys Val Ala Leu Gln Gly Leu
385                 390                 395                 400 aac aag att ttg gag gta aag aat tcg gtg act aat ctt gat ttc tcg       1248
Asn Lys Ile Leu Glu Val Lys Asn Ser Val Thr Asn Leu Asp Phe Ser
                405                 410                 415 aac tgg agg aag gaa ttg gat gag caa aag gtt aag tat ccg ttg agt       1296
Asn Trp Arg Lys Glu Leu Asp Glu Gln Lys Val Lys Tyr Pro Leu Ser
            420                 425                 430
```

```
ttt aaa aca ttt ggc gaa gct att cct ccg cag tat gcc att caa gtg    1344
Phe Lys Thr Phe Gly Glu Ala Ile Pro Pro Gln Tyr Ala Ile Gln Val
        435                 440                 445 ctt gat gag tta acg ggt ggg aat gcg att att agc act ggg gtc ggg    1392
Leu Asp Glu Leu Thr Gly Gly Asn Ala Ile Ile Ser Thr Gly Val Gly
450                 455                 460 cag cat cag atg tgg gct gct cag ttt tac aaa tac aac aag cct aga    1440
Gln His Gln Met Trp Ala Ala Gln Phe Tyr Lys Tyr Asn Lys Pro Arg
465                 470                 475                 480 caa tgg ctg acg tca ggt gga cta ggc gcg atg ggt ttt ggg ttg ccc    1488
Gln Trp Leu Thr Ser Gly Gly Leu Gly Ala Met Gly Phe Gly Leu Pro
                485                 490                 495 gct gct atc ggg gcg gct gtt gca aga cct gat gcg gta gta gtt gat    1536
Ala Ala Ile Gly Ala Ala Val Ala Arg Pro Asp Ala Val Val Val Asp
            500                 505                 510 atc gat ggt gat gga agc ttt ata atg agc gtt caa gag tta gcc aca    1584
Ile Asp Gly Asp Gly Ser Phe Ile Met Ser Val Gln Glu Leu Ala Thr
        515                 520                 525 atc cgt gtt gaa aat ctt cct gtt aag att ttg tta ctt aac aat cag    1632
Ile Arg Val Glu Asn Leu Pro Val Lys Ile Leu Leu Leu Asn Asn Gln
530                 535                 540 cat ttg ggt atg gtg gtt cag ttg gag gat cgg ttt tac aag gcg aat    1680
His Leu Gly Met Val Val Gln Leu Glu Asp Arg Phe Tyr Lys Ala Asn
545                 550                 555                 560 cgg gct cat acc tac tta gga aat ccg tca aaa gag tct gaa ata ttc    1728
Arg Ala His Thr Tyr Leu Gly Asn Pro Ser Lys Glu Ser Glu Ile Phe
                565                 570                 575 cct aac atg ttg aag ttt gct gaa gcg tgt gat atc cca gct gcc cga    1776
Pro Asn Met Leu Lys Phe Ala Glu Ala Cys Asp Ile Pro Ala Ala Arg
            580                 585                 590 gtg acc cgg aag gca gat cta cga gca gct att cag aag atg ttg gat    1824
Val Thr Arg Lys Ala Asp Leu Arg Ala Ala Ile Gln Lys Met Leu Asp
        595                 600                 605 aca ccg ggg cct tac ttg ttg gat gtg atc gtg ccc cat caa gaa cat    1872
Thr Pro Gly Pro Tyr Leu Leu Asp Val Ile Val Pro His Gln Glu His
610                 615                 620 gtg ttg ccc atg atc ccg gct ggt gga ggt ttc atg gat gtg atc acc    1920
Val Leu Pro Met Ile Pro Ala Gly Gly Gly Phe Met Asp Val Ile Thr
625                 630                 635                 640 gaa ggc gac ggc aga atg aaa tat tga                                1947
Glu Gly Asp Gly Arg Met Lys Tyr *
                645

<210> SEQ ID NO 10
<211> LENGTH: 648
<212> TYPE: PRT
<213> ORGANISM: Xanthium sp.

<400> SEQUENCE: 10

Met Ala Ala Ile Pro His Thr Asn Pro Ser Ile Thr Thr Lys Pro
 1               5                  10                  15

Ser Ser Pro Pro Arg Pro Thr Phe Leu Ala Arg Phe Thr Phe Pro Ile
                20                  25                  30

Thr Ser Thr Ser His Lys Arg His Arg Leu His Ile Ser Asn Val Leu
            35                  40                  45

Ser Asp Ser Lys Pro Thr Ile Thr His Ser Pro Leu Pro Thr Glu Ser
        50                  55                  60

Phe Ile Ser Arg Tyr Ala Pro Asp Gln Pro Arg Lys Gly Ala Asp Val
65                  70                  75                  80
```

```
Leu Val Glu Ala Leu Glu Arg Glu Gly Val Thr Asp Val Phe Ala Tyr
                85                  90                  95
Pro Gly Gly Ala Ser Met Glu Ile His Gln Ala Leu Thr Arg Ser Thr
            100                 105                 110
Thr Ile Arg Asn Val Leu Pro Arg His Glu Gln Gly Gly Val Phe Ala
        115                 120                 125
Ala Glu Gly Tyr Ala Arg Ala Ser Gly Leu Pro Gly Val Cys Ile Ala
    130                 135                 140
Thr Ser Gly Pro Gly Ala Thr Asn Leu Val Ser Gly Leu Ala Asp Ala
145                 150                 155                 160
Leu Leu Asp Ser Val Pro Met Val Ala Ile Thr Gly Gln Val Pro Arg
                165                 170                 175
Arg Met Ile Gly Thr Asp Ala Phe Gln Glu Thr Pro Ile Val Glu Val
            180                 185                 190
Thr Arg Ser Ile Thr Lys His Asn Tyr Leu Val Leu Asp Val Glu Asp
        195                 200                 205
Ile Pro Arg Ile Val Arg Glu Ala Phe Tyr Leu Ala Ser Ser Gly Arg
    210                 215                 220
Pro Gly Pro Val Leu Ile Asp Val Pro Lys Asp Ile Gln Gln Gln Leu
225                 230                 235                 240
Val Val Pro Lys Trp Asp Glu Pro Ile Arg Leu Pro Gly Tyr Leu Ser
                245                 250                 255
Arg Leu Pro Lys Thr Glu Asn Asn Gly Gln Leu Glu His Ile Val Arg
            260                 265                 270
Leu Val Ser Glu Ala Lys Arg Pro Val Leu Tyr Val Gly Gly Gly Cys
        275                 280                 285
Leu Asn Ser Gly Asp Glu Leu Arg Arg Phe Val Glu Leu Thr Gly Ile
    290                 295                 300
Pro Val Ala Ser Thr Leu Met Gly Leu Gly Ala Tyr Pro Ala Ser Ser
305                 310                 315                 320
Asp Leu Ser Leu His Met Leu Gly Met His Gly Thr Val Tyr Ala Asn
                325                 330                 335
Tyr Ala Val Asp Lys Ser Asp Leu Leu Leu Ala Phe Gly Val Arg Phe
            340                 345                 350
Asp Asp Arg Val Thr Gly Lys Leu Glu Ala Phe Ala Ser Arg Ala Lys
        355                 360                 365
Ile Val His Ile Asp Ile Asp Ser Ala Glu Ile Gly Lys Asn Lys Gln
    370                 375                 380
Pro His Val Ser Ile Cys Gly Asp Ile Lys Val Ala Leu Gln Gly Leu
385                 390                 395                 400
Asn Lys Ile Leu Glu Val Lys Asn Ser Val Thr Asn Leu Asp Phe Ser
                405                 410                 415
Asn Trp Arg Lys Glu Leu Asp Glu Gln Lys Val Lys Tyr Pro Leu Ser
            420                 425                 430
Phe Lys Thr Phe Gly Glu Ala Ile Pro Pro Gln Tyr Ala Ile Gln Val
        435                 440                 445
Leu Asp Glu Leu Thr Gly Gly Asn Ala Ile Ile Ser Thr Gly Val Gly
    450                 455                 460
Gln His Gln Met Trp Ala Ala Gln Phe Tyr Lys Tyr Asn Lys Pro Arg
465                 470                 475                 480
Gln Trp Leu Thr Ser Gly Gly Leu Gly Ala Met Gly Phe Gly Leu Pro
                485                 490                 495
Ala Ala Ile Gly Ala Ala Val Ala Arg Pro Asp Ala Val Val Val Asp
```

```
        500                 505                 510
Ile Asp Gly Asp Gly Ser Phe Ile Met Ser Val Gln Glu Leu Ala Thr
        515                 520                 525

Ile Arg Val Glu Asn Leu Pro Val Lys Ile Leu Leu Asn Asn Gln
530                 535                 540

His Leu Gly Met Val Val Gln Leu Glu Asp Arg Phe Tyr Lys Ala Asn
545                 550                 555                 560

Arg Ala His Thr Tyr Leu Gly Asn Pro Ser Lys Ser Glu Ile Phe
            565                 570                 575

Pro Asn Met Leu Lys Phe Ala Glu Ala Cys Asp Ile Pro Ala Ala Arg
            580                 585                 590

Val Thr Arg Lys Ala Asp Leu Arg Ala Ala Ile Gln Lys Met Leu Asp
            595                 600                 605

Thr Pro Gly Pro Tyr Leu Leu Asp Val Ile Val Pro His Gln Glu His
            610                 615                 620

Val Leu Pro Met Ile Pro Ala Gly Gly Phe Met Asp Val Ile Thr
625                 630                 635                 640

Glu Gly Asp Gly Arg Met Lys Tyr
                645
```

```
<210> SEQ ID NO 11
<211> LENGTH: 22
<212> TYPE: DNA
<213> ORGANISM: Artificial Sequence
<220> FEATURE:
<223> OTHER INFORMATION: Primer ALS1-1F

<400> SEQUENCE: 11
catcatcatt aaataaccag ac                                            22

<210> SEQ ID NO 12
<211> LENGTH: 22
<212> TYPE: DNA
<213> ORGANISM: Artificial Sequence
<220> FEATURE:
<223> OTHER INFORMATION: Primer ALS1-1R

<400> SEQUENCE: 12
aacccggtaa cctcatcggt tc                                            22

<210> SEQ ID NO 13
<211> LENGTH: 22
<212> TYPE: DNA
<213> ORGANISM: Artificial Sequence
<220> FEATURE:
<223> OTHER INFORMATION: Primer ALS1-2F

<400> SEQUENCE: 13
cccggttttg atagatgtac cg                                            22

<210> SEQ ID NO 14
<211> LENGTH: 22
<212> TYPE: DNA
<213> ORGANISM: Artificial Sequence
<220> FEATURE:
<223> OTHER INFORMATION: Primer ALS1-2R

<400> SEQUENCE: 14
ctgagcagcc cacatctgat gt                                            22

<210> SEQ ID NO 15
```

-continued

```
<211> LENGTH: 22
<212> TYPE: DNA
<213> ORGANISM: Artificial Sequence
<220> FEATURE:
<223> OTHER INFORMATION: Primer ALS1-3F

<400> SEQUENCE: 15
ctgagcagcc cacatctgat gt                                              22

<210> SEQ ID NO 16
<211> LENGTH: 22
<212> TYPE: DNA
<213> ORGANISM: Artificial Sequence
<220> FEATURE:
<223> OTHER INFORMATION: Primer ALS1-3R

<400> SEQUENCE: 16
aattacacaa caaaacatta ac                                              22

<210> SEQ ID NO 17
<211> LENGTH: 19
<212> TYPE: DNA
<213> ORGANISM: Artificial Sequence
<220> FEATURE:
<223> OTHER INFORMATION: Primer ALS-3F

<400> SEQUENCE: 17
gcgctgttag acagtgtcc                                                  19

<210> SEQ ID NO 18
<211> LENGTH: 18
<212> TYPE: DNA
<213> ORGANISM: Artificial Sequence
<220> FEATURE:
<223> OTHER INFORMATION: Primer SUNALS1F1

<400> SEQUENCE: 18
actaatcttg atttttcg                                                   18

<210> SEQ ID NO 19
<211> LENGTH: 20
<212> TYPE: DNA
<213> ORGANISM: Artificial Sequence
<220> FEATURE:
<223> OTHER INFORMATION: Primer ALS-6R

<400> SEQUENCE: 19
cggcagattt tcaacacgga                                                 20
```